US00RE47750E

(19) United States
(12) Reissued Patent
Phanstiel, IV et al.

(10) Patent Number: US RE47,750 E
(45) **Date of Reissued Patent: *Dec. 3, 2019**

(54) ANTI-METASTATIC AGENTS PREDICATED UPON POLYAMINE MACROCYLIC CONJUGATES

(71) Applicant: University of Central Florida Research Foundation, Inc., Orlando, FL (US)

(72) Inventors: Otto Phanstiel, IV, Oviedo, FL (US); Aaron Muth, Orlando, FL (US)

(73) Assignee: University of Central Florida Research Foundation, Inc., Orlando, FL (US)

( * ) Notice: This patent is subject to a terminal disclaimer.

(21) Appl. No.: 15/902,995

(22) Filed: Feb. 22, 2018

Related U.S. Patent Documents

Reissue of:
(64) Patent No.: 9,266,815
Issued: Feb. 23, 2016
Appl. No.: 14/388,851
PCT Filed: Mar. 13, 2013
PCT No.: PCT/US2013/031073
§ 371 (c)(1),
(2) Date: Sep. 29, 2014
PCT Pub. No.: WO2013/148219
PCT Pub. Date: Oct. 3, 2013

U.S. Applications:
(60) Provisional application No. 61/616,915, filed on Mar. 28, 2012.

(51) Int. Cl.

| | |
|---|---|
| ***C07C 211/17*** | (2006.01) |
| ***A61K 45/06*** | (2006.01) |
| ***C07C 211/36*** | (2006.01) |
| ***A61K 31/132*** | (2006.01) |

(52) U.S. Cl.
CPC ..... *C07C 211/17* (2013.01); *A61K 31/132* (2013.01); *A61K 45/06* (2013.01); *C07C 211/36* (2013.01); *C07C 2601/18* (2017.05)

(58) Field of Classification Search
CPC . C07C 211/17; C07C 211/36; C07C 2601/18; A61K 45/06; A61K 31/132
See application file for complete search history.

(56) References Cited

U.S. PATENT DOCUMENTS

| | | | | |
|---|---|---|---|---|
| 4,917,826 | A * | 4/1990 | Johnson et al. | 552/522 |
| 7,728,041 | B2 | 6/2010 | Phanstiel | |
| 9,266,815 | B2 | 2/2016 | Phanstiel, IV et al. | |
| 2007/0213397 | A1 | 9/2007 | Phanstiel | |
| 2009/0069441 | A1 | 3/2009 | Phanstiel | |
| 2009/0155265 | A1 | 6/2009 | Zeldis | |
| 2012/0015865 | A1 | 1/2012 | Zelphati et al. | |
| 2015/0057361 | A1 | 2/2015 | Phanstiel, IV et al. | |

FOREIGN PATENT DOCUMENTS

| | | |
|---|---|---|
| WO | 02/058679 | 8/2002 |

OTHER PUBLICATIONS

International Search Report and Written Opinion for PCT Application PCT/US13/031073 dated Mar. 13, 2013, pp. 1-12.
Abeloff, M. D. S., M.; Luk, G.D.; Griffin, C.A.; Hermann, J.; Blanc, O.; Sjoerdsma, A.; Baylin, S.B., Phase I trial and pharmacokinetic studies of alpha-difluoromethylornithine—an inhibitor of polyamine biosynthesis. *Journal of Clinical Oncology* 1984, 2, 124-130.
American Cancer Society. Cancer facts & figures 2012.
Asaki, T.; Hamamoto, T.; Sugiyama, Y.; Kuwano, K.; Kuwabara, K., Structure-activity studies on diphenylpyrazine derivatives: A novel class of prostacyclin receptor agonists. Bioorganic and Medicinal Chemistry Letters 2007, 15, 6692-6704.
Azmi, A. S. A., A.; Banerjee, S.; Rangnekar, V.M.; Mohammad, R.M.; Sarkar, F.H., Chemoprevention of pancreatic cancer: Characterization of Par-4 and its modulation by 3,3' diindolylmethane (DIM). Pharmaceutical Research 2008, 25, 2117-2124.
Baetz, K. M., L.; Gable, K.; Tamsin, T.; Reberioux, D.; Bryan, J.; Andersen, R.J.; Dunn, T.; Hieter, Roberge, M., Yeast genome-wide drug-induced haploinsufficiency screen to determine drug mode of action. PNAS 2004, 101, 4525-4530.
Barreiro, E. J.; Kummerle, A. E.; Fraga, C. A. M., The methylation effect in medicinal chemistry. Chemical Reviews 2011.
Basu Roy, U. K. R., Nathaniel S.; Kachel, Karen L.; Gerner, Eugene W., Activated K-RAS increases polyamine uptake in human colon cancer cells through modulation of caveolar endocytosis. Molecular Carcinog. 2008, 47, 538-553.
Basuroy, U. K. G., E.W., Emerging concepts in targeting the polyamine metabolic pathway in epithelial cancer chemoprevention and chemotherapy. Journal of Biochemistry 2006, 139, 27-33.
Belting, M.; Persson, S.; Fransson, L.-A., Proteoglycan involvement in polyamine uptake. Biochem. J. 1999, 338, 317-323.
Belting, M. M., K.; Jonsson, M.; Cheng, F.; Sandgren, S.; Jonsson, S.; Ding, K.; Delcros, J-G.; Fransson, L-A., Glypican-1 is a vehicle for polyamine uptake in mammalian cells: A pivotal role for nirosothiol-derived nitric oxide. The Journal of Biological Chemistry 2003, 278, 47181-47189.
Bergeron, R. J.; McManis, J. S.; Weimar, W. R.; Schreier, K.; Gao, F.; Wu, Q.; Ortiz-Ocasio, J.; Luchetta, G.; Porter, C.; Vinson, J. R., The role of charge in polyamine analogue recognition. Journal of Medicinal Chemistry 1995, 38, 2278- 2285.
Bergeron, R. J.; Feng, Y.; Weimar, W. R.; McManis, J. S.; Dimova, H.; Porter, C. W.; Raisler, B.; Phanstiel, O., A comparison of structure-activity relationships between spermidine and spermine analogue antineoplastics. Journal of Medicinal Chemistry 1997, 40, 1475-1494.

(Continued)

*Primary Examiner* — Jerry D Johnson
(74) *Attorney, Agent, or Firm* — Timothy H. Van Dyke; Beusse, Wolter, Sanks & Maire PLLC

(57) ABSTRACT

Disclosed herein are novel motuporamine compounds that act as anti-metastatic agents with low toxicity and high anti-migration activity. The non-toxic, anti-metastatic agents may be given to patients with potential or actual metastatic cancers, such as pancreatic cancers, alone in combination with known and/or new therapies to help block the growth and spread of tumor(s).

9 Claims, 6 Drawing Sheets

(56) References Cited

OTHER PUBLICATIONS

Breitbeil, F.; Kaur, N.; Delcros, J.-G.; Martin, B.; Abboud, K. A.; Phanstiel, O., Modeling the preferred shapes of polyamine transporter ligands and dihydromotuporamine-C mimics: Shovel versus hoe. Journal of Medicinal Chemistry 2006, 49, 2407-2416.
Burns, M. R. C., C. Lance; Vanderwerf, Scott M.; Ziemer, Josh R.; Weeks, Reitha S.; Cai, Feng; Webb, Heather K.; Graminski, Gerard F., Amino acid/spermine conjugates: Polyamine amides as potent spermidine uptake inhibitors. Journal of Medicinal Chemistry 2001, 44, 3632-3644.
Burns, M. R.; Graminski, G. F.; Weeks, R. S.; Chen, Y.; O'Brien, T. G., Lipophilic lysine-spermine conjugates are potent polyamine transport inhibitors for use in combination with a polyamine biosynthesis inhibitor. Journal of Medicinal Chemistry 2009, 52, 1983-1993.
Byers, T. L.; Wechter, R.; Nuttall, M. E.; Pegg, A. E., Expression of a human gene for polyamine transport in chinese hamster ovary cells. Biochem. J. 1989, 263, 745-752.
Casero, R. A.; Celano, P.; Ervin, S. J.; Wiest, L.; Pegg, A. E., High specific induction of spermidine/spermine N1-acetyltransferase in a human large cell lung carcinoma. Biochem. J. 1990, 270, 615-620.
Chen, Y. W., R.S.; Burns, M.R.; Boorman, D.W.; Klein-Szanto, A., Combination therapy with 2-difluoromethylornithine and a polyamine transport inhibitor against murine squamous cell carcinoma. Int. J. Cancer 2006, 118, 2344-2349.
Coleman, C. S.; Pegg, A. E., Polyamine analogues inhibit the ubiquitination of spermidine/spermine N1-acetyltransferase and prevent its targeting to the proteasome for degradation. Biochem. J. 2001, 358, 137-145.
Covassin, L. D., M.; Charest-Gaudreault, R.; Audette, M.; Bonneau, M.-J.'; Poulin, R., Synthesis of spermidine and norspermidine dimers as high affinity polyamine transport inhibitors. Bioorg. Med. Chem. Lett. 1999, 9, 1709-1714.
Cullis, P. M.; Green, R. E.; Merson-Davies, L.; Travis, N., Probing the mechanism of transport and compartmentalization of polyamines in mammalian cells. Chem. Biol. 1999, 6, 717-729.
Delcros, J.-G. T., S.; Carrington, S.; Martin, B.; Renault, J.; Blagbrough, I.S.; Uriac, P., Effect of spermine conjugation on the cytotoxicity and cellular transport of acridine. Journal of Medicinal Chemistry 2002, 45, 5098-5111.
Ellenbroek, S. C., J., RhoGTPases: functions and associations with cancer. Clin. Exp. Metastasis 2007, 24 (8), 657-672.
Fabian, C. J. K., B.F.; Brady, D.A.; Mayo, M.S.; Chang, C.H.; Ferraro, J.A.; Zalles, C.M.; Stanton, A.L.; Masood, S.; Grizzle, W.E.; Boyd, N.F.; Arneson, D.W.; Johnson, K.A., A Phase II breast cancer chemoprevention trial of oral alpha-difluoromethylornithine: Breast tissue, imaging, and serum and urine biomarkers. Clinical Cancer Research 2002, 8, 3105-3117.
Flescher, E. B., T.L.; Ballester, A.; Houk, R.; Talal, N., Increased polyamines may downregulate interleukin 2 production in rheumatoid arthritis. J. Clin. Invest. 1989, 83, 1356-1362.
Flescher, E. B., T.L.; Talal, N., Polyamine oxidation down-regulates IL-2 production by human peripheral blood mononuclear cells. The Journal of Immunology 1989, 142, 907-912.
Flescher, E. F., D.; Talal, N., Polyamine-dependent production of lymphocytotoxic levels of ammonia by human peripheral blood monocytes Immunology Letters 1991, 28, 85-90.
Fogel-Petrovic, M.; Shappell, N. W.; Bergeron, R. J.; Porter, C. W., Polyamine and polyamine analog regulation of spermidine/spermine N1-acetyltransferase in MALME-3M human melanoma cells. The Journal of Biological Chemistry 1993, 268, 19118-19125.
Fogel-Petrovic, M.; Kramer, D. L.; Vujcic, S.; Miller, J.; McManis, J. S.; Bergeron, R. J.; Porter, C. W., Structural basis for differential induction of spermidine/spermine N1-Acetyltransferase activity by novel spermine analogs. Molecular Pharmacology 1997, 52, 69-74.
Furstner, A.; Rumbo, A., Ring-closing alkyne metathesis. Stereoselective synthesis of the cytotoxic marine alkaloid motuporamine C. The Journal of Organic Chemistry 2000, 65, 2608-2611.
Gahl, W. A.; Pitot, H. C., Reversal by aminoguanidine of the inhibition of proliferation of human fibroblasts by spermidine and spermine. Chem.-Biol. Interact. 1978, 22, 91-98.
Gardner, R. A.; Kinkade, R.; Wang, C.; Phanstiel, O. I., Total synthesis of petrobactin and its homologues as potential growth stimuli for Marinobacter hydrocarbonclasticus, an oil-degrading bacteria. The Journal of Organic Chemistry 2004, 69, 3530-3537.
Gardner, R. A.; Delcros, J.-G.; Konate, F.; Breitbeil, F.; Martin, B.; Sigman, M.; Phanstiel, O., N1-Substituent effects in the selective delivery of polyamine-conjugates into cells containing active polyamine transporters. Journal of Medicinal Chemistry 2004, 47, 6055-6069.
Gerner, E. W. M., F.L., Polyamines and cancer: old molecules, new understanding. Nature Reviews Cancer 2004, 4, 781-792.
Gerner, E. W. M., F.L.; Goldschmid, S.; Lance, P.; Pelot, D., Rationale for, and design of, a clinical trial targeting polyamine metabolism for colon cancer chemoprevention. Amino Acids 2007, 33, 189-195.
Goldring, W. P. D. W., Larry, Cytotoxic Alkaloids Motuporamines A-C: Synthesis and Structural Verification. Organic Letters 1999, 1 (9), 1471-1473.
Heaton, M. A. F., Wayne F., Methylglyoxal-bis(guanylhydrazone)-Resistant Chinese Hamster Ovary Cells: Genetic Evidence That More Than A Single Locus Controls Uptake. Journal of Cellular Physiology 1988, 136, 133-139.
Hibshoosh, H. J., M.; Weinstein, I.B., Effects of overexpression of ornthine decarboxylase (ODC) on growth control and oncogene-induced cell transformation. Oncogene 1991, 6, 739-743.
Kane, B. E.; Grant, M. K. O.; El-Fakahany, E. E.; Ferguson, D. M., Synthesis and evaluation of xanomeline analogs—Probing the wash-resistant phenomenom at the M1 muscarinic acetylcholine receptor. Bioorganic and Medicinal Chemistry Letters 2008, 16, 1376-1392.
Kaur, N.; Delcros, J.-G.; Martin, B.; Phanstiel, O., Synthesis and biological evaluation of dihydromotuporamine derivatives in cells containing active polyamine transporters. Journal of Medicinal Chemistry 2005, 48, 3832-3839.
Kaur, N.; Delcros, J.-G.; Imran, J.; Khaled, A.; Chehtane, M.; Tschammer, N.; Martin, B.; Phanstiel, O. IV, A comparison of chloroambucil- and xylene-containing polyamines leads to improved ligands for accessing the polyamine transport system. Journal of Medicinal Chemistry 2008, 51, 1393-1401.
Kaur, N.; Delcros, J.-G.; Archer, J.; Weagraff, N. Z.; Martin, B.; Phanstiel, O. I., Designing the polyamine pharmacophore: Influence of N-substituents on the transport behavior of polyamine conjugates. Journal of Medicinal Chemistry 2008, 51, 2551-2560.
Kemmer, D. M., L.M.; Hoon, S.; Reberioux, D.; Giaever, G.; Nislow, C.; Roskelley, C.D.; Roberge, M., Combining chemical genomics screens in yeast to reveal spectrum of effects of chemical inhibition of sphingolipid biosynthesis. BMC Microbiology 2009, 9, 9-26.
Kramer, D. L.; Miller, J. T.; Bergeron, R. J.; Khomutov, R.; Khomutov, A.; Porter, C. W., Regulation of polyamine transport by polyamines and polyamine analogues. J. Cell. Physiol. 1993, 155, 399-407.
Kramer, D. L.; Fogel-Petrovic, M.; Diegelman, P.; Cooley, J. M.; Bernacki, R. J.; McManis, J. S.; Bergeron, R. J.; Porter, C. W., Effects of novel spermine analogues on cell cycle progression and apoptosis in MALME-3M human melanoma cells. Cancer Research 1997, 57, 5521-5527.
Kramer, D. L.; Vujcic, S.; Diegelman, P.; Alderfer, J.; Miller, J.; Black, J. D.; Bergeron, R. J.; Porter, C. W., Polyamine analogue induction of the p53-p21WAF1/CIP1-Rb pathway and G1 arrest in human melanoma cells. Cancer Research 1999, 59, 1278-1286.
Kruczynski, A.; Vandenberghe, I.; Pillon, A.; Pesnel, S.; Goetsch, L.; Barret, J.-M.; Guminski, Y.; Le Pape, A.; Imbert, T.; Bailly, C.; Guilbaud, N., Preclinical activity of F14512, designed to target tumors expressing an active polyamine transport system. Invest. New Drugs 2011, 29, 9-21.
Laduron, F.; Tamborowski, V.; Moens, L.; Horvath, A.; De Smaele, D.; Leurs, S., Efficient and scalable method for the selective alkylation and acylation of secondary amines in the presence of primary amines Organic Process Research and Development 2005, 9, 102-104.

(56) References Cited

OTHER PUBLICATIONS

Mandel, J. L.; Flintoff, W. F., Isolation of mutant mammalian cells altered in polyamine transport. J. Cell. Physiol. 1978, 97, 335-344.
Meyskens Jr, F. L. G., E.W. , Development of Difluoromethylornithine (DFMO) as a chemoprevention agent. Clinical Cancer Research 1999, 5, 945-951.
Middleton, R.; Briddon, S.; Cordeaux, Y.; Yates, A.; Dale, C.; George, M.; Baker, J.; Hill, S.; Kellam, B., New fluorescent adenosine A1-receptor agonists that allow quantification of ligand-receptor interactions in microdomains of single living cells. Journal of Medicinal Chemistry 2007, 50, 782-793.
Morgan, D. M., Polyamine oxidases and oxidized polyamines. In Physiology of Polyamines, Bachrach, U.; Heimer, Y. M., Eds. CRC Press: Boca Raton, FL, 1989; vol. 1, pp. 203-229.
Mosmann, T., Rapid colorimetric assay for cellular growth and survival: Application to proliferation and cytotoxic assays. J. Immunol. Methods 1983, 65, 55-63.
Palmer, A. J. W., H.M., The polyamine transport system as a target for anticancer drug development. Amino Acids 2010, 38, 415-422.
Phanstiel, O.; Price, H. L.; Wang, L.; Juusola, J.; Kline, M.; Shah, S. M., The effect of polyamine homologation on the transport and cytotoxicity properties of polyamine-(DNA intercalator) conjugates. . The Journal of Organic Chemistry 2000, 65, 5590-5599.
Phanstiel, O. I.; Kaur, N.; Delcros, J.-G., Structure-activity investigations of polyamine-anthracene conjugates and their uptake via the polyamine transporter. Amino Acids 2007, 33, 305-313.
Phanstiel, O. A., J.J., Design of polyamine transport inhibitors as therapeutics. In Polyamine Drug Discovery, 1 ed.; Casero, R. W., P., Ed. Royal Society of Chemistry: 2011; p. 302.
Prugh, J.; Birchenough, L.; Egberton, M., A simple method of protecting a secondary amine with tert butyloxycarbonyl (BOC) in the presence of a primary amine. Synthetic Communications 1992, 22, 2357-2360.
Roberge, M., Defining drug targets in yeast haploinsufficiency screens: application to human translational pharmacology. Sci. Signal. 2008, 1, pt5.
Roskelley, C. D.; Williams, D. E.; McHardy, L. M.; Leong, K. G.; Armelle, T.; Karsan, A.; Andersen, R. J.; Dedhar, S.; Roberge, M., Inhibition of tumor cell invasion and angiogenesis by motuporamines. Cancer Research 2001, 61, 6788-6794.
Seiler, N.; Dezeure, F., Polyamine transport in mammalian cells Int. J. Biochem. 1990, 22, 211-218.
Seiler, N.; Delcros, J.-G.; Moulinoux, J. P., Polyamine transport in mammalian cells. An update. Int. J. Biochem. 1996, 28, 843-861.
Seiler, N. D., B.; Gosse, F.; Raul, F., Spermine cytotoxicity to human colon carcinoma-derived cells (CaCo-2). Cell Biology and Toxicology 2000, 16, 117-130.
Seiler, N., Thirty years of polyamine-related approaches to cancer therapy. Retrospect and prospect. Part 2. Structural analogues and derivatives. Current Drug Targets 2003, 4, 537-564.
Shrestha, A. S., D.; Malladi, S. S.; Warshakoon, H. J.; David, S. A., Structure-activity relationships of lipopolysaccharide sequestration in N-alkylpolyamines. Bioorg. Med. Chem. Lett. 2009, 19, 2478-2481.
Soulet, D. C., L.; Kaouass, M.; Charest-Gaudreault, R.; Audette, M.; Poulin, R., Role of endocytosis in the internalization of spermidine-C(2)-BODIPY, a highly fluorescent probe of polyamine transport. Biochem. J. 2002, 367, 347-357.
Soulet, D. G., B.; Rivest, S.; Audette, M.; Poulin, R., A fluorescent probe of polyamine transport accumulates into intracellular acidic vesicles via a two-step mechanism. The Journal of Biological Chemistry 2004, 279, 49355-49366.
Suzuki, O. M., T.; Katsumata, Y., Determination of polyamine oxidase activities in human tissues. Experientia 1984, 40, 838-839.
To, K. C. W. L., K. T.; Roskelley, C. D.; Andersen, R. J.; O'Connor, T. P., The anti-invasive compound motuporamine C is a robust smitulator of neuronal growth cone collapse. Neuroscience 2006, 139, 1263-1274.
Vial, E. S., E.; Marshall, C. J., ERK-MAPK signaling coordinately regulates activity of Rac1 and RhoA for tumor cell motility. Cancer Cell 2003, 4 (1), 67-79.
Wallick, C. J. G., I.; Thorne, M.; Feith, D.J.; Takasaki, K.Y.; Wilson, S.M.; Seki, J.A.; Pegg, A.E.; Byus, C.V.; Bachmann, A.S., Key role for p27Kip1, retinoblastoma protein Rb, and MYCN in polyamine inhibitor-induced G1 cell cycle arrest in MYCN-amplified human neuroblastoma cells. Oncogene 2005, 24, 5606-5618.
Wang, L.; Price, H. L.; Juusola, J.; Kline, M.; Phanstiel, O. I., Influence of polyamine architecture on the transport and topoisomerase II inhibitory properties of polyamine DNA-intercalator conjugates. Journal of Medicinal Chemistry 2001, 44, 3682-3691.
Wang, C.; Delcros, J.-G.; Biggerstaff, J.; Phanstiel, O., Synthesis and biological evaluation of N1-(anthracen-9-ylmethyl)triamines as molecular recognition elements for the polyamine transporter. Journal of Medicinal Chemistry 2003, 46, 2663-2671.
Wang, C.; Delcros, J.-G.; Biggerstaff, J.; Phanstiel, O., Molecular requirements for targeting the polyamine transport system: Synthesis and biological evaluation of polyamine anthracene conjugates. Journal of Medicinal Chemistry 2003, 46, 2672-2682.
Wang, C.; Delcros, J.-G.; Cannon, L.; Konate, F.; Carias, H.; Biggerstaff, J.; Gardner, R. A.; Phanstiel, O., Defining the molecular requirements for the selective delivery of polyamine conjugates into cells containing active polyamine transporters. Journal of Medicinal Chemistry 2003, 46, 5129-5138.
Welch, S. C. L., J-P., Reduction of [(phenylthio)methyl]carbinyl benzoate esters to alkenes with titanium metal. J. Org. Chem. 1981, 46, 4072-4076.
Williams, D. E. L., P.; Andersen, R.J., Motuporamines A-C, cytotoxic alkaloids isolated from the marine sponge Xestospongia exigua (Kirkpatrick). Journal of Organic Chemistry 1998, 63, 4838-4841.
Williams, D. E.; Craig, K. S.; Patrick, B.; McHardy, L. M.; van Soest, R.; Roberge, M.; Andersen, R. J., Motuporamines, anti-invasion and anti-angiogenic alkaloids from the marine sponge Xestospongia exigua (Kirtpatrick): Isolation, structure elucidation, analogue synthesis, and conformational analysis. The Journal of Organic Chemistry 2002, 67, 245-258.
Fabian, C. et al., "A Phase II breast cancer chemoprevention trial of oral alpha-difluoromethylornithine: Breast tissue, imaging, and serum and urine biomarkers", Clinical Cancer Research, 2002, vol. 8, pp. 3105-3117.
McHardy, L. M. "A study of the mechanism of action of novel inhibitors of tumour cell invasion", The University of British Columbia, Vancouver, British Columbia, 2007, 163 pages.
Straatman, K., "Wound healing assay", In http://www.le.ac.uk/biochem/microscopy/wound-healing-assay.html, University of Leicester, U.K., 2008.
International Search Report and Written Opinion, PCT/US2013/031073, Aug. 8, 2013.

* cited by examiner

ANTI-METASTATIC AGENTS PREDICATED UPON POLYAMINE MACROCYLIC CONJUGATES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a U.S. National Stage application of PCT Application No. PCT/US13/31073 filed Mar. 13, 2013. This application is related to U.S. Provisional Application No. 61/616,915 filed Mar. 28, 2012. Priority is claimed to the foregoing under 35 USC 120 and 119.

FIELD OF THE INVENTION

The present invention relates to novel, non-toxic, anti-metastatic compounds, and to pharmaceutical compositions comprising the compounds, and to methods for their use in the treatment or prevention of metastatic cancers.

BACKGROUND

In 1998, Andersen et al reported the discovery of the motuporamine family of compounds from the sea sponge Xestespongia exigua off the coast of Motupore Island in Papua New Guinea.[36] These compounds were of particular interest as they each possessed a large macrocycle tethered to a norspermidine (3,3-triamine) message. This class of drug was structurally similar to anthryl-polyamines previously reported by Phanstiel et. al.[9,36] Biologically, dihydromotuporamine C (44a) proved to be the most interesting as it was highly cytotoxic to the MDA-231 breast carcinoma cells and had good anti-invasive properties.[36-37] Due to the motuporamine compounds exhibiting structural similarities to 5a (Ant33) and other analogues made previously in our lab[9], it was thought that they may function in a similar manner to anthryl-polyamine conjugates. Structures of motuporamine natural products (41, 42, 43, 44a) and dihydromotuporamine C mimic (45) and Ant33 (5a) are as follows:

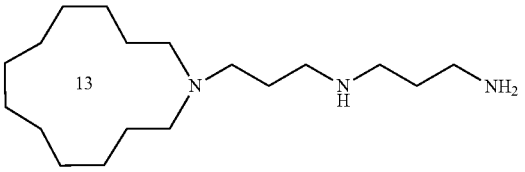

41: Motuporamine A

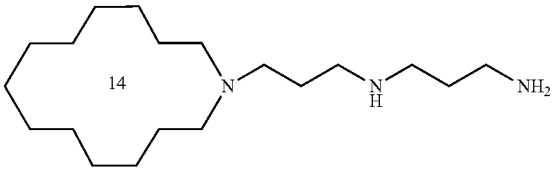

42: Motuporamine B

-continued

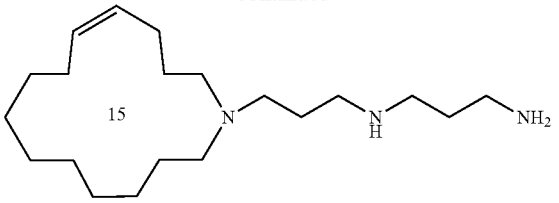

43: Motuporamine C

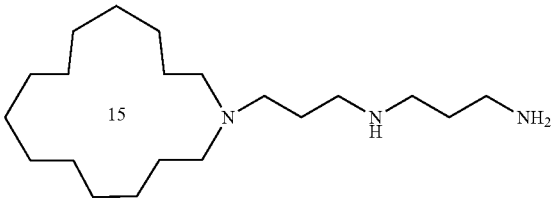

44a: Dihydromotuporamine C (Motu33)

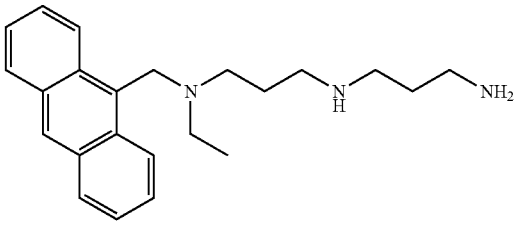

45: AntNEt33

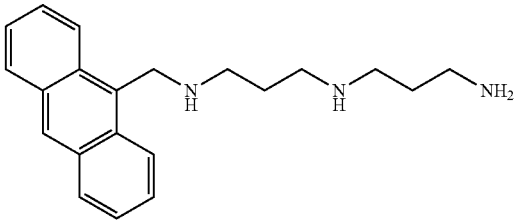

5a: Ant33

Note: the Ring size is noted by the number inside the macrocycle.

Recently, it has been shown that dihydromotuporamine C (44a) affects the sphingolipid biosynthetic pathway.[38] Baetz et. al initially showed through a genome-wide haploinsufficiency screen in yeast that dihydromotuporamine C targets sphinoglipid metabolism.[38a] This was demonstrated via the recognized sensitivity of genes LCB1 and TSC10 to the addition of dihydromotuporamine C. Both are key genes involved in the biosynthesis of sphingosine, which is a sphingolipid precursor.[38a] This was the first molecular target described for 44a. The authors went on to demonstrate that dihydromotuporamine C at 60 μM was able to fully inhibit the growth of yeast cells.[39] However, the addition of an intermediate of the sphingosine and ceramide pathway (dihydrosphingosine) to dihydromotuporamine C-treated yeast cells, was able to rescue this growth inhibition.[39] While it was shown that dihydromotuporamine C directly lowers the levels of ceramide, the addition of exogenous ceramide was able to partially rescue yeast growth indicating that dihydromotuporamine directly targets sphingolipid biosynthesis.[38] Despite this finding in yeast, it could not be demonstrated that exogenous ceramide could completely rescue the effects of dihydromotuporamine C.[38a,b] This observation could be explained by dihydromotuporamine C having multiple targets in human cells or that the rescue event was limited by the amount of ceramide that could be added as ceramide is known to have pro-apoptotic properties.[38a,b] The fact that the less toxic dihydrsphingosine could rescue these cells is consistent with the latter possibility.

Beyond sphingolipid metabolism, Rho GTPase was also identified as a target of dihydromotuporamine C (44a).[38b] An increase in Rho signaling has been associated with many types of cancer.[40] This increase in Rho signaling has also seen to play a part in the anti-invasive action of dihydromotuporamine C.[38b,41] This has been partly explained by a loss of cell polarity and an increase in adhesion strength caused by Rho activation.[38b] Another key player in the anti-migration ability of dihydromotuporamine C is the activation of integrin signaling, which in turn leads to the inhibition of tumor migration by activated Rho signaling.[38b, 42]

A series of structure activity relationship studies has also helped determine which aspects of dihydromotuporamine C's (44a) structure provides its unique biological activity. The structure of the motuporamines can be broken into two main areas: the macrocyclic ring, and the norspermidine tail. It has been shown that the 15-membered macrocyclic ring is favored over other size rings as it demonstrated the highest levels of cytotoxicity and invasion inhibition in MDA-MB-231 cells.[37a] Williams et. al. also showed that the degrees of unsaturation in the ring also dramatically affected the biological activity of the series, where a saturated ring (completely void of unsaturation) proved to be most biologically interesting in terms of anti-migration properties.[37a] A carbazole ring substitute also showed promising anti-invasion properties, although it was not as potent as the parent, dihydromotuporamine C.[37a]

The other key structural characteristic of the motuporamines is the norspermidine tail. It was demonstrated that acetylation of the terminal amino group had no effect on the biological activity of motuporamine C (43), however, acetylation of both amine groups saw a complete loss of activity.[37b] This finding points to the importance of the central secondary amine for these compounds to exhibit high biological activity.

Previous efforts by Phanstiel et. al. explored the conformational preferences of dihydromotuporamine C (44a) by computer modeling.[43] These experiments demonstrated that the saturated ring system was conformationally mobile as expected. The orientation of the polyamine chain off the ring was shown to be critical and helped the authors design new motuporamine mimics These mimics were predicated upon anthryl-polyamines Specifically, AntNEt33 (45) had similar computed molecular conformation preferences to dihydromotuporamine C (44a) and was shown to mimic the cytotoxicity of dihydromotuporamine C in CHO and CHO-MG. See U.S. Pat. No. 7,728,041, the entirety of which is hereby incorporated by reference. Also ref: "Modeling the Preferred Shapes of Polyamine Transporter Ligands and Dihydromotuporamine-C Mimics: Shovel versus Hoe," Breitbeil III, F. Kaur, N.; Delcros, J-G.; Martin, B.; Abboud, K. A.; Phanstiel, I V, O. J. Med. Chem. 2006, 49, 2407-2416. Although AntNEt33 (45) was a good mimic of dihydromotuporamine C in vitro, it failed to mimic the anti-metastatic properties of dihydromotuporamine C in vivo.

DETAILED DESCRIPTION OF THE INVENTION

Figure 1:
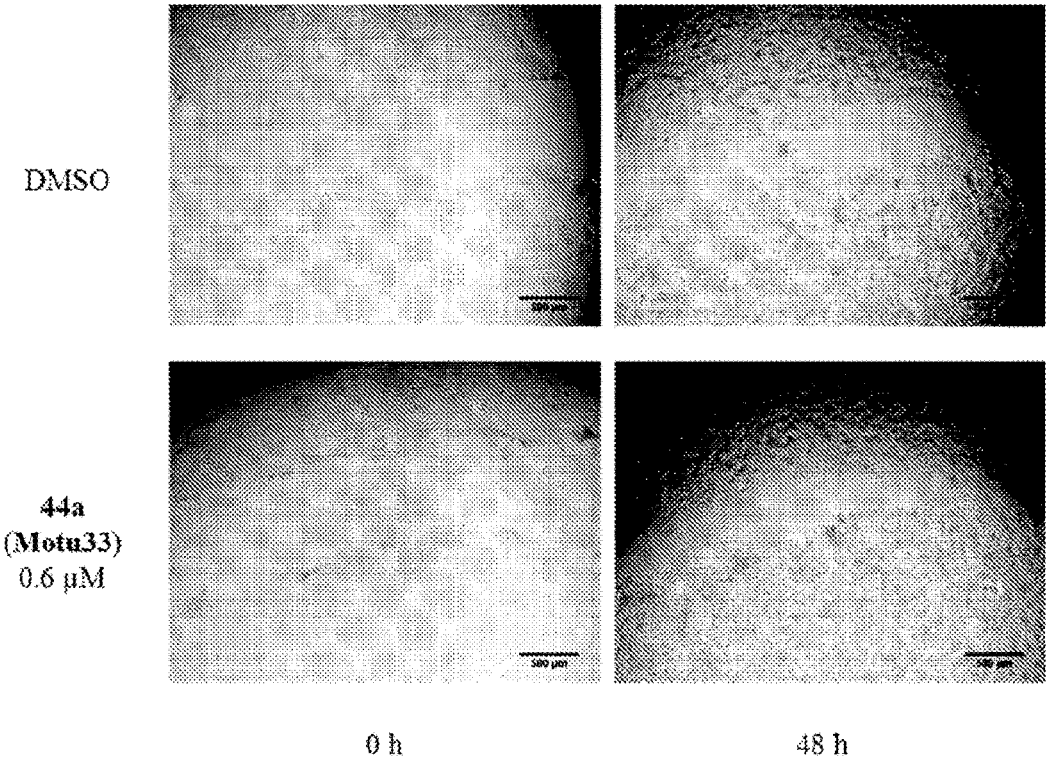
FIG. 1 shows L3.6p1 Cell Migration with 44a (Motu33) via Wound Healing Assay[a,b] [a]L3.6p1 cells were incubated with 250 μM AG for 24 h prior to drug addition. [b]Cells were incubated for 48 h at 37° C. with the respective conjugate.

The present inventors have developed new motuporamine analogues, which modulate the cytotoxicity of this drug class while simultaneously enhancing their anti-migration ability. In summary, by incrementally moving the polyamine chain outside the ring, new compounds were discovered which increased the anti-migration potency and reduced toxicity relative to the parent compound 44a. These compounds innovatively extend the polyamine motif away from the macrocycle and use a carbocycle (all carbon-containing ring) over the nitrogen-containing heterocycle of the parent compound 44a. This is a clear advantage as the 15-membered ketone is commercially available and avoids a lengthy synthesis of the heterocycle, which is not commercially available (See Synthesis and Biological Evaluation of Dihydromotuporamine Derivatives in Cells Containing Active Polyamine Transporters" Kaur, N; Delcros, J-G.; Martin, B.; Phanstiel, IV, O. J. Med. Chem. 2005, 48, 3832-3839).

Further, the present inventors have found a dramatic increase in the therapeutic window available to these new agents relative to the parent compound 44a. These large carbocycles (e.g., the macrocyclic core) and carbocycle-alkyl groups (e.g., cyclopentadecyl-$CH_2$—is preferred) represent a new N-substituent which imparts the unique properties of anti-migration activity and lower toxicity. Advantageously, the compounds described herein may be administered alone or in combination with known and/or new therapies (e.g., other chemotherapeutic agents or radiation) to help treat or prevent the spread of primary tumors and allow time for the intervention (e.g., other chemotherapeutic) to work on the primary tumor. Moreover, preliminary results indicate that the compounds by themselves have been shown to significantly shrink tumor mass compared to untreated controls in a pancreatic cancer model using L3.6p1 cells in mice.

In accordance with one aspect, there are provided new chemical entities that move the polyamine outside the macrocycle structure having the formula:

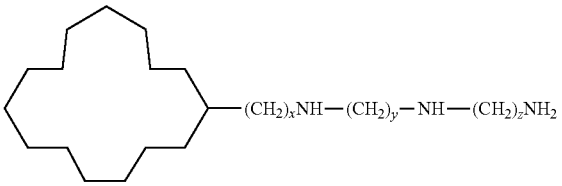

wherein x=0-6;

wherein y=3 or 4 or 5; and wherein z=3 or 4 or 5;

or an analog, a derivative, a prodrug, a stereoisomer, or a pharmaceutically acceptable salt thereof.

In one embodiment, x=1; y=3; and z=3 such that the compound comprises structure (47a):

(II)

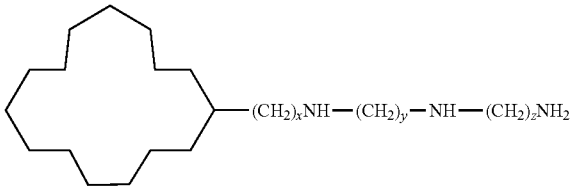

47a: x=1, y=3, z=3 or an analog, a derivative, a prodrug, a stereoisomer, or a pharmaceutically acceptable salt thereof.

In another embodiment, x=1; y=4; and z=4 such that the compound comprises structure (47b):

(III)

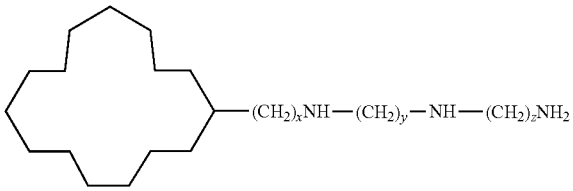

47b: x=1, y=4, z=4 or an analog, a derivative, a prodrug, a stereoisomer, or a pharmaceutically acceptable salt thereof.

In another aspect, there is provided a pharmaceutical composition comprising a pharmaceutically acceptable carrier and a compound of formula (I) above. In one embodiment, the compound comprises compound 47a. In another embodiment, the compound comprises compound 47b.

In another aspect, there is provided a method for preventing or treating a cancer in a subject comprising administering to a subject a composition comprising a compound of formula (I) above in an amount effective to inhibit metastatic activity or tumor growth in the subject. In one embodiment, the cancer is pancreatic cancer. In another embodiment, the cancer is breast cancer.

In another aspect, there is provided a method for preventing or treating pancreatic cancer in a subject. The method comprises administering to a subject a composition comprising a compound of formula (I) in an amount effective to inhibit metastatic activity or tumor growth in the subject.

In another aspect, there is provided a method for preventing or treating breast cancer in a subject comprising administering to a subject a composition comprising a compound of formula (I) in an amount effective to inhibit metastatic activity or tumor growth in the subject.

In another aspect, there is provided a method for inhibiting acid sphingomyelinase (ASM) activity in a subject comprising administering to a subject a composition comprising a compound of claim 1 in an amount effective to inhibit ASM activity in the subject.

In accordance with another aspect, there are provided new chemical entities of the following formulas:

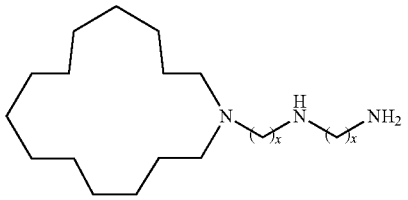

44a: x=3; 3 HCl (Motu33)
44b: x=4; 3 HCl (Motu44)

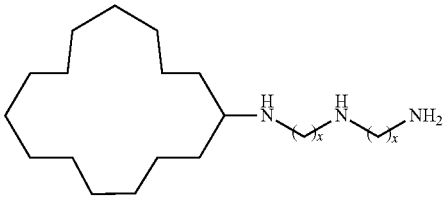

46a: x=3; 3 HCl (MotuN33)
46b: x=4; 3 HCl (MotuN44)

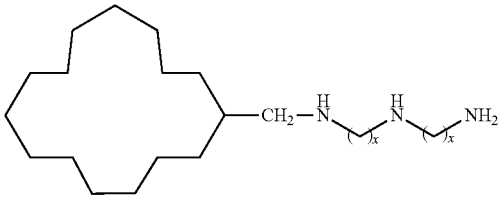

47a: x=3; 3 HCl ($MotuCH_2N33$)
47b: x=4; 3 HCl ($MotuCH_2N44$)

The above compounds (including 47a, 47b) were then screened in cell-based assays to evaluate their cytotoxicity and ability to target cells via the polyamine transport system using their appended polyamine motif. As shown in Table 1 below, as the polyamine motif was moved incrementally outside the ring (44a→46a→47a) the cytotoxicity was dramatically reduced. A similar trend was observed in the series: 45b→46b→47b. This was observed uniformly across three cell lines. L3.6p1 is a metastatic human pancreatic cancer cell line, CHO-MG* is a Chinese hamster ovary cell line with mutations which make its polyamine transport system defective and CHO is the wild-type Chinese hamster ovary cell line. Drugs which target the polyamine transport system should be toxic to CHO but less so to CHO-MG* and should give a high CHO-MG*/CHO $IC_{50}$ ratio. None of the drugs tested 44(a and b)-47(a and b) demonstrated significant selectivity in targeting CHO over CHOMG* cells and all were deemed not polyamine-transport selective by this assay (Table 1).

While the polyamine transport system targeting was disappointing, the lower toxicity observed in the extended compounds 47a and 47b in L3.6p1 were encouraging (Table 2). The different toxicity observed in the L3.6p1 line was promising because it demonstrated that the parent drug's cytotoxicity could be modulated by extending the polyamine chain away from the macrocycle. ($IC_{50}$ comparisons 44a: 0.99 μM versus 47a: 89.4 μM; Table 2). The $IC_{50}$ value is the concentration of the drug needed to inhibit 50% of the relative cell population. A low $IC_{50}$ value indicates a more toxic drug as less of the drug is needed to inhibit cell growth.

The drug panel was then assayed for its ability to inhibit the migration of L3.6p1 cells in a plastic well after a 48 hour incubation period at 37° C. Having determined the cytotoxicity of each drug, the respective maximum tolerated doses (MTD) were determined. This allowed all drugs to be assessed at MTD concentrations in which they did not kill cells but instead inhibited cell migration. In addition, each drug was tested at the MTD of the parent compound (0.6 μM) to allow for direct comparisons of potency. Critically, as shown in Table 3, compound 47a had a significant improvement in anti-migration ability vs. the parent 44a, when dosed at the same low dose of 0.6 μM. Compound 47a was also significantly less toxic than the parent (44a) as well (about 130 times less toxic) and represents one of several new compounds with improved properties over the parent compound. Further, preliminary studies show the compound 47a not only inhibited migration of cancerous cells, but was also shown to inhibit tumor growth in vivo in mouse studies. Compounds 46a, 46b, and 47a have this anti-migration property as well, and are also of interest.

In addition to 47a, 47b, aspects of the present invention contemplate a family of structurally related compounds having the formula (which includes 47a and 47b):

(I)

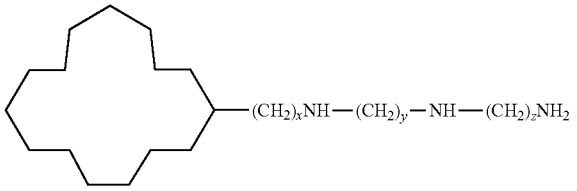

wherein x=0-6;
wherein y=3 or 4 or 5; and
wherein z=3 or 4 or 5;
or a pharmaceutically acceptable salt thereof.

As was shown above in Table 1 below, as the polyamine motif was moved incrementally outside the ring (44a→46a→47a) the cytotoxicity was dramatically reduced. A similar trend was observed in the series: 45b→46b→47b. While not wishing to be bound by any mechanistic theory, it is believed that polyamine may be moved out to x=6 before the molecule reaches an undesirable level of toxicity. Further, while still providing useful compounds, it was found that as x and/or y increases from x=3 and y=3, generally, an increase in toxicity may be seen. For example, the 4,4-analogue 47b (CHO $IC_{50}$: 47.8 μM) (where x and y=4) was roughly twice as toxic as the 3,3-analogue 47a (CHO $IC_{50}$: 82.9 μM) (where x and y=3). It is recognized that additional analogues could also involve y=2 and/or z=2 spacer units. These systems, however, will significantly perturb the pKa of the amine centers and are considered less preferred.

In addition, effective compounds may also be realized by modifying the terminal amine group ($RNH_2$). For example, Anderson et al found that terminal N-acetylation provided compounds with similar activity to the non-N-acetylated derivatives. (see refs 36. and 37(a))

We found that N-methylation provides enhanced drug stability to amine oxidases. In this regard, derivatives which cap the N-terminus with an acyl group (e.g., acetyl) or alkyl group (e.g. methyl) may provide further enhancements based upon findings in related systems.

(IV)

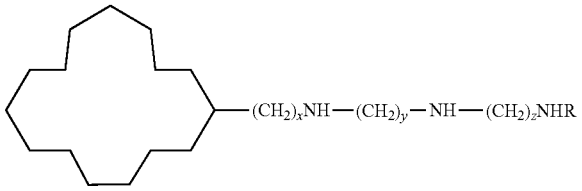

wherein x=0-6;
wherein y=3 or 4 or 5; and
wherein z=3 or 4 or 5;
R=acyl, or alkyl
or a pharmaceutically acceptable salt thereof. Reference to alkyl herein may in a more specific embodiment refer to a straight or branched-chain C1-C10 alkyl group. Reference to acyl herein refers to H—C(O)—, alkyl-C(O)— or cycloalkyl-C(O)—. In one embodiment, acyls contain a lower alkyl. Non-limiting examples of suitable acyl groups include formyl, acetyl and propanoyl.

In a specific embodiment, x=1, y=z=3 and R=acetyl; or x=1, y=z=3 and R=Me.

Alternatively, the polyamine sequence could be truncated to give shortened analogues such as:

(V)

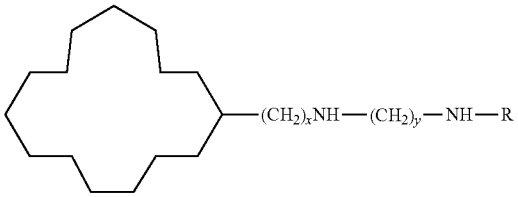

wherein x=0-6;
wherein y=3 or 4 or 5 or 6 or 7 or 8;
R=hydrogen, acyl, or alkyl
or a pharmaceutically acceptable salt thereof. Acyl and alkyl are the same as that described for formula IV.

In a specific embodiment, x=1, y=3 and R=acetyl; or x=1, y=3 and R=Me
or a pharmaceutically acceptable salt thereof

1.1 Definitions

The compounds according to formula (I) referred to herein, as well as compounds 46a, 46b, include those compounds and any analog, derivative, prodrug, stereoisomer, or pharmaceutically acceptable salt thereof. Thus, by "by compounds of formula (I)" "compounds according to formula (I)," or the like, it is meant the compounds according to the formula or any analog, derivative, prodrug, stereoisomer, or pharmaceutically acceptable salt thereof. The compounds according to formula (I), as well as compounds 46a, 46b may be collectively referred to as "anti-metastatic agents" or individually as "an anti-metastatic agent."

As used herein, the terms "about" and "approximately" as used herein refers to values that are ±10% of the stated value.

As used herein, the terms "administering" or "administration" of a compound or agent as described herein to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the term "analog" refers to a compound having a structure similar to that of another one, but differing from it with respect to a certain component. The compound may differ in one or more atoms, functional groups, or substructures, which may be replaced with other atoms, groups, or substructures. In one aspect, such structures possess at least the same or a similar therapeutic efficacy.

The term "cancer" as used herein refers to a physiological condition in mammals that is typically characterized by unregulated cell growth. Exemplary cancers include, but are not limited to carcinoma, lymphoma, blastoma, sarcoma, and leukemia. More particularly, examples of such cancers include lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma.

As used herein, the terms "co-administered, "co-administering," or "concurrent administration", when used, for example with respect to administration of a conjunctive agent along with administration of a composition as described herein refers to administration of an anti-metastatic agent as described herein and a conjunctive agent such that both can simultaneously achieve a physiological effect. The two agents, however, need not be administered together. In certain embodiments, administration of one agent can precede administration of the other, however, such co-administering typically results in both agents being simultaneously present in the body (e.g. in the plasma) of the subject.

As used herein, "derivative" refers to a compound derived or obtained from another and containing essential elements of the parent compound. In one aspect, such a derivative possesses at least the same or similar therapeutic efficacy as the parent compound.

As used herein, the terms "disease," "disorder," or "complication" refers to any deviation from a normal state in a subject. In preferred embodiments, the methods and compositions of the present invention are useful in the diagnosis and treatment of diseases characterized at least in part by cell proliferation and/or differentiation where control of polyamine transport is required.

As used herein, by the term "effective amount," "amount effective," "therapeutically effective amount," or the like, it is meant an amount effective at dosages and for periods of time necessary to achieve the desired result.

As used herein, the term "metastases" or "metastatic" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location.

As used herein, term "pharmaceutically acceptable salt" is intended to include art-recognized pharmaceutically acceptable salts. These non-toxic salts are usually hydrolyzed under physiological conditions, and include organic and inorganic acids and bases. Examples of salts include sodium, potassium, calcium, ammonium, copper, and aluminum as well as primary, secondary, and tertiary amines, basic ion exchange resins, purines, piperazine, and the like. The term is further intended to include esters of lower hydrocarbon groups, such as methyl, ethyl, and propyl.

As used herein, the terms "composition" or "pharmaceutical composition" comprises one or more of the compounds described herein (e.g., the compounds of formula (I) or 46a, 46b or "an anti-metastatic agent) as active ingredient(s), or a pharmaceutically acceptable salt(s) thereof, and may also contain a pharmaceutically acceptable carrier and optionally other therapeutic ingredients. The compositions include compositions suitable for oral, rectal, ophthalmic, pulmonary, nasal, dermal, topical, parenteral (including subcutaneous, intramuscular and intravenous) or inhalation administration. The most suitable route in any particular case will depend on the nature and severity of the conditions being treated and the nature of the active ingredient(s). The compositions may be presented in unit dosage form and prepared by any of the methods well-known in the art of pharmacy. Dosage regimes may be adjusted for the purpose to improving the therapeutic response. For example, several divided dosages may be administered daily or the dose may be proportionally reduced over time. A person skilled in the art normally may determine the effective dosage amount and the appropriate regime.

As used herein, the term "preventing" means causing the clinical symptoms of a disorder or disease state, e.g., cancer, not to develop, e.g., inhibiting the onset of disease, in a subject that may be exposed to or predisposed to the disease state, but does not yet experience or display symptoms of the disease state.

As used herein, the term "prodrug" refers to a compound that is converted to a therapeutically active compound after administration, and the term should be interpreted as broadly herein as is generally understood in the art. Generally, but not necessarily, a prodrug is inactive or less active than the therapeutically active compound to which it is converted.

As used herein, the term "stereoisomer" refers to a compound which has the identical chemical constitution, but differs with regard to the arrangement of the atoms or groups in space. It is appreciated with respect to the compounds of formula (I) and 46a, and 46b, the polyamine chain is not limited to extending from a particular location the ring as shown herein and that the polyamine arm may extend from any position on the 15-membered ring.

As used herein, term "subject" refers to any animal (e.g., a mammal), including, but not limited to, humans, which may be the recipient of a particular treatment. The term is intended to include living organisms susceptible to conditions or diseases caused or contributed to by unrestrained cell proliferation and/or differentiation where control of polyamine transport is required. Examples of subjects include humans, dogs, cats, cows, goats, and mice. As used herein, the terms "treating" or "treatment" refers to both therapeutic treatment and prophylactic or preventative measures, wherein the object is to prevent or slow down (lessen) the targeted pathologic condition or disorder.

1.2 Pharmaceutical Compositions

The compositions described herein may comprise an anti-metastatic agent as described herein. In one embodiment, there are provided pharmaceutical compositions comprising a compound of formula (I) above, or an analog, a derivative, a prodrug, a stereoisomer, or a pharmaceutically acceptable salt thereof, which can be administered to a patient to achieve a therapeutic effect, e.g., inhibit polyamine transport activity in the cells of a subject. In a particular embodiment, the pharmaceutical compound comprises compound 47a, or an analog, a derivative, a prodrug, a stereoisomer, or a pharmaceutically acceptable salt thereof. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones, such as anticancer agents.

In addition to the active ingredients, these pharmaceutical compositions can contain suitable pharmaceutically acceptable carriers comprising excipients and auxiliaries, which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the crosslinked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push fit capsules made of gelatin, as well as soft, sealed capsules made of gelatin and a coating, such as glycerol or sorbitol. Push fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 150 mM histidine, 0.1%2% sucrose, and 27% mannitol, at a pH range of 4.5 to 5.5, which is combined with buffer prior to use.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

1.3 Determination of a Therapeutically Effective Dose

The determination of a therapeutically effective dose is well within the capability of those skilled in the art. A therapeutically effective dose refers to that amount of active ingredient which causes cytotoxicity of cancer cells in a subject and/or metastatic behavior which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies may be used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The toxicity of the present compounds of this invention can be further modulated by terminal N-acylation and or alkylation. For example, polyamine compounds containing N-methyl groups are most stable to amine oxidases and are less toxic (see Designing the Polyamine Pharmacophore: Influence of N-substituents on the transport behavior of polyamine conjugates, Kaur, N.; Delcros, J-G.; Archer, J.; Weagraff, N. Z.; Martin, B.; Phanstiel IV, O. J. Med. Chem. 2008, 51, 2551-2560.). The parent compound 44a has been shown to retain its anti-migration properties after terminal N-acetylation. These insights can be applied to the other compounds described herein.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of container and labeled for treatment of an indicated condition. Such labeling would include amount, frequency, and method of administration.

Normal dosage amounts can vary from 0.1 to 100,000 micrograms, up to a total dose of about 1 g, depending upon the route of administration and duration of therapy. Guidance as to particular dosages and methods of delivery is provided in the literature and generally available to practitioners in the art. Those skilled in the art will employ different formulations for nucleotides than for proteins or their inhibitors.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, mammals such as dogs, cats, cows, horses, rabbits, monkeys, and most preferably, humans.

1.4 Applications

The compositions and methods described herein may be useful for the treatment and/or prevention of a cancer. In one embodiment, the methods and compositions may be utilized for the treatment of a metastatic cancer. It is appreciated that the cancer being treated may already have metastasized or is potentially metastatic. The cancer may comprise non-solid tumors, e.g., leukemia, multiple myeloma, hematologic malignancies or lymphoma. In another embodiment, the cancer is characterized by solid tumors and their potential or actual metastases including, but not limited to, melanoma; non-small cell lung cancer; glioma; hepatocellular (liver) carcinoma; glioblastoma; carcinoma and tumors of the thyroid, bile duct, bone, gastric, brain/CNS, head and neck; and hepatic, stomach, prostrate, breast, renal, testicular, ovarian, skin, cervical, lung, muscle, neuronal, esophageal, bladder, lung, uterine, vulval, endometrial, kidney, colorectal, pancreatic, pleural/peritoneal membranes, salivary gland, and epidermoid.

In one embodiment, the cancer is breast cancer. In another embodiment, the cancer is pancreatic cancer. Referring to FIG. 7, FIG. 7 shows orthotopic mouse model experiments where human pancreatic cancer L3.6p1 cells were injected into a mouse pancreas and the degree of metastasis was measured via liver micrometastases: x axis=drug used to inhibit metastases; y-axis=# of micrometastases per slide. The control was saline solution. The respective drugs (44a and 45) were dosed at their respective maximum tolerated dose (MTD). As shown, 44a was effective in reducing the degree of metastasis of L3.6p1 cells.

1.5 Conjunctive Delivery

In accordance with another aspect, there is provided a method for preventing or treating a cancer in a subject. The method comprises (a) administering to a subject a composition comprising a compound according to formula (I) in an amount effective to inhibit metastatic activity in the subject; and (b) administering at least one of radiation or a cytotoxic chemotherapeutic agent to the subject in an amount effective to induce a cytotoxic effect in cancer cells of the subject. The administering steps (a) and (b) may comprise inserting a delivery mechanism into the subject. The delivery mechanism comprises a structure insertable into the subject through which the composition can be delivered and an actuating mechanism for directing the composition into the subject. The use of such a delivery mechanism may be applied to any other embodiment of a method for treating a subject described herein as well.

The delivery mechanism may be any suitable structure known in the art, such as a syringe having a needle insertable into the subject and a plunger. Instead of a syringe, other delivery mechanisms may be used for the intermittent or continuous distribution of the compositions, such as infusion pumps, syringe pumps, intravenous pumps or the like. Typically, these mechanisms include an actuating mechanism, e.g., a plunger or pump, for directing a composition into the subject. In one embodiment, a structure, e.g., catheter or syringe needle, which may be inclusive of or separate from the delivery mechanism, is first inserted into the subject and the composition is administered through the structure through activation of the actuating mechanism.

As explained herein, the compounds have been shown to exhibit exceptional anti-metastatic activity with low toxicity. Thus, in certain embodiments, the one or more anti-metastatic agents of the present invention may be administered to a subject in combination with a known therapy to help block the spread of a tumor and allow time for another therapy therapy to work on the tumor. In one embodiment, the tumor is a primary tumor. When the cancer being prevented or treated herein is pancreatic cancer, the conjunctive therapy may comprise radiation, Whipple surgery, and/or administration of chemotherapeutic agents, including targeted therapies, such as Fluorouracil, Erlotinib Hydrochloride, Gemcitabine Hydrochloride, Mitozytrex (Mitomycin C), Mutamycin (Mitomycin C), or Tarceva (Erlotinib Hydrochloride).

When the cancer being prevented or treated herein is breast cancer, the conjunctive therapy may comprise radiation, surgery, and/or administration of chemotherapeutic agents, including targeted therapies, such as Abitrexate (Methotrexate), Abraxane (Paclitaxel Albumin-stabilized Nanoparticle Formulation), Adriamycin PFS (Doxorubicin Hydrochloride)
Adriamycin RDF (Doxorubicin Hydrochloride), Adrucil (Fluorouracil), Anastrozole, Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride Efudex (Fluorouracil), Ellence (Epirubicin Hydrochloride), Epirubicin Hydrochloride, Exemestane, Fareston (Toremifene), Faslodex (Fulvestrant), Femara (Letrozole), Fluorouracil, Folex (Methotrexate), Folex PFS (Methotrexate), Fulvestrant, Gemzar (Gemcitabine Hydrochloride), Ixabepilone, Ixempra (Ixabepilone), Lapatinib Ditosylate Letrozole, Methotrexate, Methotrexate LPF (Methotrexate), Mexate (Methotrexate), Mexate-AQ (Methotrexate), Neosar (Cyclophosphamide), Nolvadex (Tamoxifen Citrate), Novaldex (Tamoxifen Citrate), Paclitaxel, Paclitaxel Albumin-stabilized Nanoparticle Formulation Tamoxifen Citrate, Taxol (Paclitaxel), Taxotere (Docetaxel), Toremifene, Tykerb (Lapatinib Ditosylate), or Xeloda (Capecitabine).

In one embodiment, a composition comprising the anti-metastatic agents may be delivered to the subject along with another chemotherapeutic agent or therapy as is known in the art for treating the particular type of cancer. In one embodiment, the one or more anti-metastatic agents described herein can be used in conjunction with other known therapeutic/cytotoxic agents. PCT application no. PCT/US10/35800 is referred to as a resource of such chemotherapeutic agents, and is incorporated herein by reference. In one embodiment, the conjunctive agent comprises one or more cytotoxic chemotherapeutic agents shown to have been mutagenic, carcinogenic and/or teratogenic, either in treatment doses in in vivo or in vitro studies.

The mode of administration for a conjunctive formulation in accordance with the present invention is not particularly limited, provided that the composition comprising one or more of the anti-metastatic agents described herein and the conjunctive agent are combined upon administration. Such an administration mode may, for example, be (1) an administration of a single formulation obtained by formulating one or more of the anti-metastatic agents and the conjunctive agent simultaneously; (2) a simultaneous administration via an identical route of the two agents obtained by formulating one or more of the anti-metastatic agents and a conjunctive agent separately; (3) a sequential and intermittent administration via an identical route of the two agents obtained by formulating one or more the anti-metastatic agents and a conjunctive agent separately; (4) a simultaneous administration via different routes of two formulations obtained by formulating one or more of the anti-metastatic agents and a conjunctive agent separately; and/or (5) a sequential and intermittent administration via different routes of two formulations obtained by formulating one or more of the anti-metastatic agents and a conjunctive agent separately (for example, one or more of the anti-metastatic agents followed by a conjunctive agent or its composition, or inverse order) and the like.

The dose of a conjunctive formulation may vary depending on the formulation of the one or more anti-metastatic agents and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When one or more of the anti-metastatic agents and a conjunctive agent are administered to a subject, the agents may be administered at the same time, but it is also possible that the conjunctive agent is first administered and then the one or more anti-metastatic agents is administered, or that the one or more anti-metastatic agents is first administered and then the conjunctive agent is administered. When such an intermittent administration is employed, the time interval may vary depending on the active ingredient administered, the dosage form and the administration mode, and for example, when the conjunctive agent is first administered, the one or more anti-metastatic agents may be administered within 1 minute to 3 days, preferably 10 minutes to 1 day, more preferably 15 minutes to 1 hour after the administration of the conjunctive agent. When the one or more anti-metastatic agents is first administered, for example, then the one or more anti-metastatic agents may be administered within 1 minute to 1 day, preferably 10 minutes to 6 hours, more preferably 15 minutes to 1 hour after the administration of the one or more anti-metastatic agents.

It is understood that when referring to the one or more anti-metastatic agents and a conjunctive agent, it is meant the one or more anti-metastatic agents alone, a conjunctive agent alone, as a part of a composition, e.g., composition, which optionally includes one or more pharmaceutical carriers. It is also contemplated that more than one conjunctive agent may be administered to the subject if desired.

EXAMPLES

1.6 Synthesis

The synthesis of 44a was previously described by Goldring et. al.[44], Fürstner et. al.[45] Williams et. al.[37a], and Kaur et. al.[2f], while the synthesis of 44b was previously described by Kaur et. al.[2f].

The syntheses of the four remaining compounds began with the synthesis of 46a and 46b. As shown in Scheme III-1, reductive amination of commercially available ketone 48 with Boc-protected polyamines (49a or 49b)[34, 46] gave the respective compounds 50a and 50b in moderate yield (54% and 75%, respectively). These two compounds were then each treated with 4 M HCl in EtOH to remove the Boc groups and provided 46a and 46b in high yield (98% and 99%, respectively). The overall yields for compounds 46a and 46b were 53% and 74%, respectively, from ketone 48.

In contrast, the synthesis of the extended motifs 47a and 47b proved to be more challenging as the generation of aldehyde 53 was more difficult than initially thought (Scheme 2). The first attempt at generating aldehyde 53 was through the use of (methoxymethyl)triphenylphosphonium chloride in a classic Wittig reaction to generate the vinyl ether, followed by hydrolysis. Generation of the vinyl ether failed while trying several base sources (BuLi, NaHMDS, NaH) where only the starting ketone 48 was recovered. The second attempt utilized Vilsmeier-Haack conditions with $POCl_3$ in DMF to generate (Z)-2-chlorocyclopentadec-1-enecarbaldehyde followed by reduction with $H_2$ and Pd/C. The alkene intermediate was generated fairly smoothly, albeit at 70% conversion. The subsequent reduction method was unsuccessful at reducing the alkene intermediate to the final desired aldehyde 53. While it was unclear why these methods failed, steric crowding may play a role.

After two unsuccessful attempts at generating aldehyde 53, a longer synthetic route was chosen. This route began with commercially available ketone 48 and a standard Wittig reaction with methyltriphenylphosphonium iodide, to generate alkene 51 in 69% yield. Alkene 51 was then subjected to hydroboration conditions, followed by oxidation of the resultant alcohol with PCC to generate aldehyde 53 which was used without further purification. Reductive amination of aldehyde 53 with Boc-protected polyamines 49a and 49b generated 54a and 54b in 36% and 51%, respectively. These Boc-protected compounds were then deprotected with 4 M HCl to give 47a and 47b in 92% and 95% yields, respectively. The overall yields of 47a and 47b were 17% and 21% respectively from ketone 48.

Scheme 1.[a] Synthesis of 46a and 46b

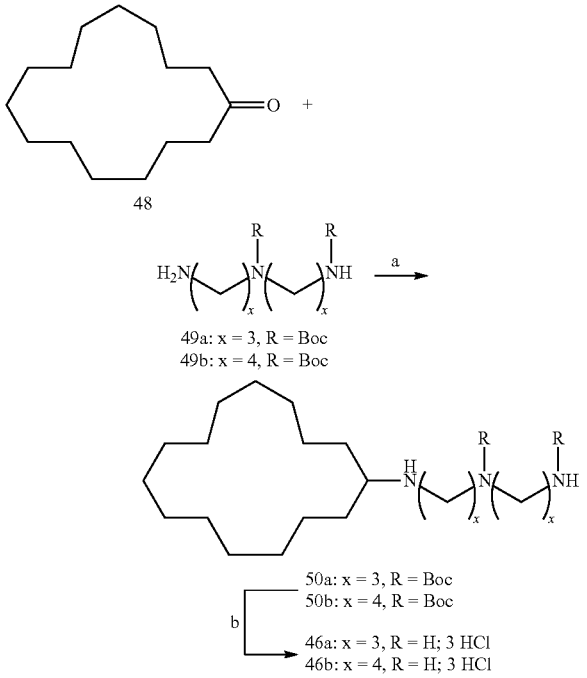

[a]Reagent: (a) $NaBH(OAc)_3$, AcOH, $CH_2Cl_2$; (b) 4M HCl, EtOH

Scheme 2.[a] Synthesis of 47a and 47b

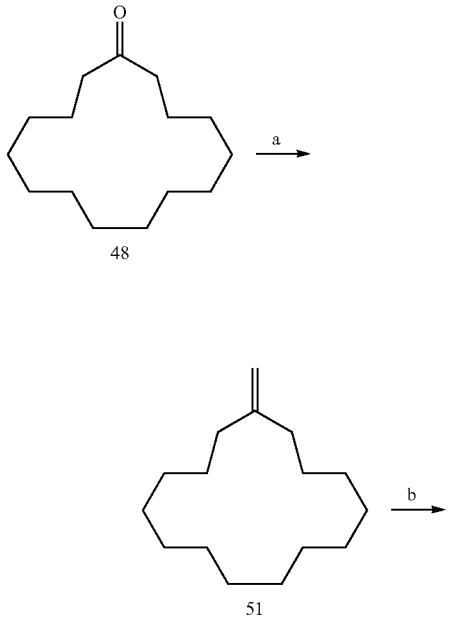

-continued

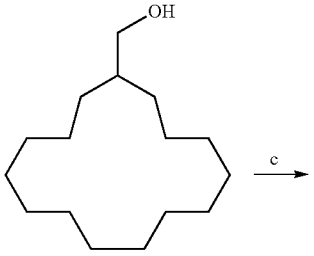

52

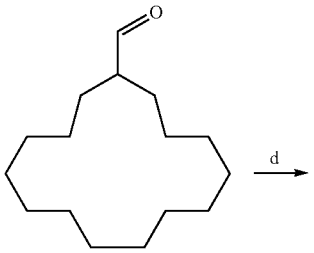

53

-continued

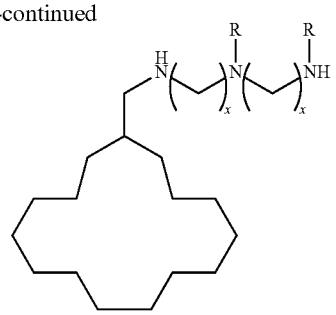

54a: x = 3, R = Boc
54b: x = 4, R = Boc e

47a: x = 3, R = H; 3 HCl
47b: x = 4, R = H; 3 HCl

[a]Reagent: (a) $Ph_3PCH_3I$, BuLi, THF, 0° C.; (b)$BH_3$—THF, 0° C. then $H_2O_2$, 3M NaOH, RT; (c) PCC, $CH_2Cl_2$; (d) 49a[46] or 49b[34], $NaBH(OAc)_3$, AcOH, $CH_2Cl_2$; (e) 4M HCl, EtOH Other compounds of Formula (I) could be made from the same sequence of steps starting from aldehyde 53. The carbon homologation process is stepwise and could generate each of the series claimed in Formula (I) by incrementally changing the value of x. The respective BOC-substituted polyamines could be made by methods similar to those used to access 49a and 49b (see refs 46 and 34).

Formula (IV) and (V) could also be made by these methods. For example, the N-acylated derivatives where R=acyl could be made via the monoacylation of the respective diamine prior to coupling to the respective aldehyde. The terminal N-methyl derivatives would require additional protection (e.g. BOC) of the terminal amine center (e.g., $NH_2$—$(CH_2)$y-N(BOC)—$(CH2)_z$N(BOC)Me.

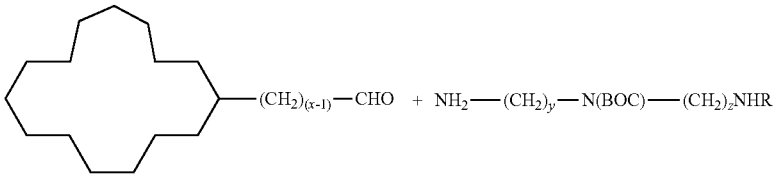

x = 0-6
Note: when x = 0, the macrocyclic ketone is employed for that synthetic step.

a

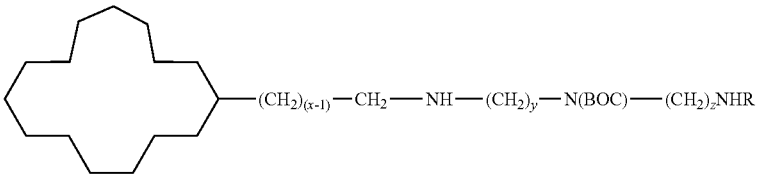

b

Compounds of Formula IV

Reagents: a) $NaBH_4$ in 50% $CH_2Cl_2$/MeOH; b) 4M HCl

-continued

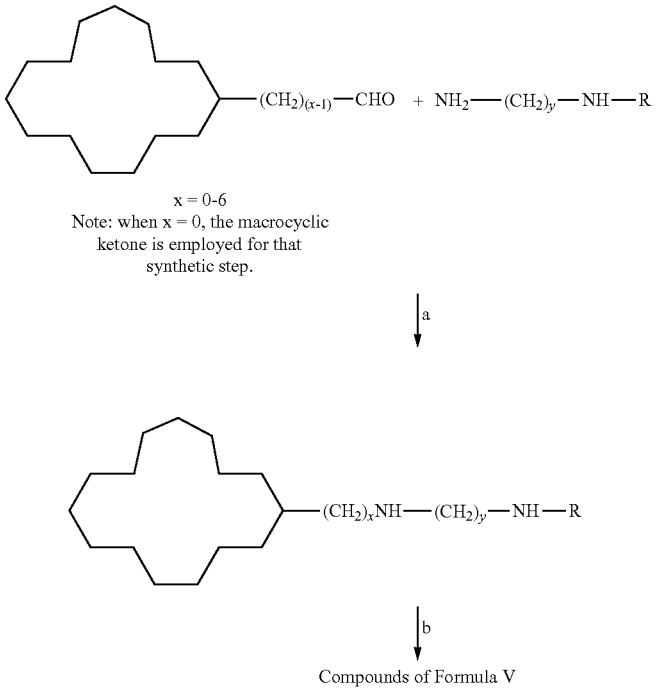

Reagents: a) $NaBH_4$ in 50% $CH_2Cl_2$/MeOH; b) 4M HCl

1.7 Biological Evaluation

Once synthesized, the conjugates were screened for toxicity in L3.6p1, CHO, and CHO-MG cells. L3.6p1 cells were selected as a human metastatic pancreatic cancer cell line. CHO cells were chosen along with a mutant PTS deficient line (CHO-MG*) in order to comment on polyamine transport selectivity.[2c-e, 6] The CHO/CHO-MG* results are shown in Table 1 below.

1.8 CHO and CHO-MG* Studies. $IC_{50}$ and MTD Determinations

CHO cells were chosen along with a mutant cell line (CHO-MG*) to comment on how the synthetic conjugates gain access to the cells.[2c-e, 6] As discussed earlier, the CHO-MG* cell line is polyamine-transport deficient and represents a model for alternative modes of entry (other than PTS) including passive diffusion or use of another transporter. The CHO cell line on the other hand, represents cells with high polyamine transport activity.[7b, 10c] A comparison of toxicity in these two CHO cell lines allowed for a screen that would detect selective use of the polyamine transporter. High utilization of the PTS would be very toxic to CHO cells. However, the CHO-MG* cells should be less sensitive to drugs which target the PTS.[2c-e, 6] Ultimately, a CHO-MG*/CHO $IC_{50}$ ratio was determined to assess PTS selectivity. A high $IC_{50}$ ratio (>>2) would be observed for PTS selective compounds.

TABLE 1

Biological Evaluation of Motuporamine Derivatives (44a-b, 46a-b, and 47a-b) in CHO and CHO-MG* Cells[a,b,c,d]

| Cmpd | CHO-MG* $IC_{50}$ (μM) | CHO $IC_{50}$ (μM) | CHO-MG*/CHO $IC_{50}$ ratio |
|---|---|---|---|
| 44a (Motu33) | 2.96 (±0.1) | 2.90 (±0.2) | 1 |
| 44b (Motu44) | 4.67 (±0.9) | 4.38 (±0.3) | 1 |
| 46a (MotuN33) | 5.95 (±0.5) | 2.84 (±0.2) | 2.1 |
| 46b (MotuN44) | 5.18 (±0.9) | 4.53 (±0.2) | 1 |
| 47a (Motu$CH_2$33) | 87.3 (±11) | 82.9 (±20) | 1 |
| 47b (Motu$CH_2$44) | 45.5 (±1.4) | 47.8 (±2.4) | 1 |

[a]CHO and CHO-MG* cells were incubated with 1 mM AG for 24 h prior to drug addition.
[b]The ratio denotes the (CHO-MG*/CHO) $IC_{50}$ ratio, a measure of PTS selectivity.
[c]Cells were incubated for 48 h at 37° C. with the respective conjugate.
[d]All experiments were run in triplicate.

As reported earlier, dihydromotuporamine C (44a) and its analogue 44b did not exhibit PTS selectivity as their $IC_{50}$ ratio in the original CHO-MG line and CHO were both 1.[2f] This was verified again to be the case in CHO and CHO-MG*. Indeed, both 44a and 44b exhibited a CHO-MG*/CHO $IC_{50}$ ratio of 1. Low $IC_{50}$ ratio were observed for analogues 46a, 46b, 47a, and 47b demonstrating a general lack of PTS selectivity.

Despite this apparent lack of PTS selectivity, an interesting general trend in cytotoxicity was observed in both CHO and CHO-MG*. As the amine at the $N^1$ position was moved away from the macrocyclic core, the cytotoxicity decreased. This was most dramatic for 47a and 47b where a methylene spacer was present between the amine at the $N^1$ position and the macrocyclic core. It is also interesting to note that the 4,4-analogue 47b (CHO $IC_{50}$: 47.8 μM) was roughly twice as toxic as the 3,3-analogue 47a (CHO $IC_{50}$: 82.9 μM).

1.9 L3.6p1 Studies. $IC_{50}$ and MTD Determinations

Compounds 44a-b, 46a-b and 47a-b were also tested in the metastatic human pancreatic cancer cell line, L3.6p1.[30b,35] This cell line was also chosen due to its K-RAS mutation which has been linked to increased polyamine uptake.[30b,35] This increase in polyamine uptake lends itself to being exploited by polyamine-based drug conjugates. These two features made this cell line an ideal candidate for evaluating potentially anti-metastatic polyamine-based drug conjugates. When compounds 44a-b, 46a-b, and 47a-b were initially tested in L3.6p1 their $IC_{50}$ values (Table III-2) were nearly identical to the $IC_{50}$ values found in CHO and CHO-MG*. These $IC_{50}$ results were again interesting as they showed that as the polyamine message was moved from the macrocyclic core, the cytotoxicity decreased, and was most evident for 47a and 47b. The MTD (Maximum tolerated dose) was determined for each of these compounds (Table III-2). This information was important as it allowed each compound's anti-migration properties to be assessed at its own MTD and also at the MTD of the parent compound, 44a (0.6 μM) in subsequent wound healing assays.

TABLE 2

Biological Evaluation of Motuporamine Derivatives (44a-b, 46a-b, and 47a-b) in L3.6pl Cells[a,b,c]

| Cmpd | L3.6pl $IC_{50}$ (μM) | L3.6pl MTD (μM) |
|---|---|---|
| 44a (Motu33) | 0.99 (±0.07) | 0.6 |
| 44b (Motu44) | 1.76 (±0.2) | 1.0 |
| 46a (MotuN33) | 2.81 (±0.2) | 2.0 |
| 46b (MotuN44) | 2.82 (±0.1) | 2.0 |
| 47a ($MotuCH_2$33) | 89.4 (±5.4) | 80 |
| 47b ($MotuCH_2$44) | 48.7 (±2.8) | 40 |

[a]L3.6pl cells were incubated with 250 μM AG for 24 h prior to drug addition.
[c]Cells were incubated for 48 h at 37° C. with the respective conjugate.
[d]All experiments were run in triplicate.
Note:
Steep cytotoxicity curves were observed and as a result the MTD are often near the respective $IC_{50}$ values.

1.10 Wound Healing Assay

A wound healing assay was employed to evaluate the anti-migration properties of compounds 44a-b, 46a-b, and 47a-b in L3.6p1 cells. This involved growing a monolayer of L3.6p1 cells and then scraping the monolayer with a sterile pipet tip to create a cell free zone in the middle of the well. The experiment was run in 96-well plate format. Wound healing was measured by time-course imaging of each well using a computer-controlled microscope with an x,y,z stage which allowed for reproducible imaging over time. Each drug was evaluated for its dose-dependent inhibition of cell migration. Each compound was evaluated at its own MTD in order to avoid cytotoxic effects which are well known to bias migration studies.[37a] In addition, each compound was also tested at the MTD of 44a (Motu33) in order to directly compare the potency of these compounds at the same concentration. These findings are reported in Table 3.

TABLE 3

Inhibition of L3.6pl Cell Migration by Compounds 44a-b, 46a-b, and 47a-b[a-e]

| Cmpd | Concentration (μM) | % Cell Migration | % Cell Migration Inhibition |
|---|---|---|---|
| Control | Untreated | 47.4 (±2.7) | 0 (±1.5) |
| 44a (Motu33) | 0.6[c] | 37.8 (±3.3) | 20.3 (±1.8) |
| 44b (Motu44) | 0.6 | 39.5 (±2.0) | 16.7 (±0.8) |
| | 1[c] | 33.4 (±5.1) | 29.6 (±4.5) |
| 46a (MotuN33) | 0.6 | 38.2 (±2.5) | 19.3 (±1.3) |
| | 2[c] | 31.8 (±0.1) | 32.9 (±0.1) |
| 46b (MotuN44) | 0.6 | 32.5 (±4.3) | 31.4 (±4.1) |
| | 2[c] | 31.6 (±0.5) | 33.4 (±0.5) |
| 47a ($MotuCH_2$33) | 0.6 | 29.2 (±3.2) | 38.4 (±4.2) |
| | 80[c] | 26.2 (±1.3) | 44.8 (±2.2) |
| 47b ($MotuCH_2$44) | 0.6 | 33.4 (±1.8) | 29.6 (±1.6) |
| | 40[c] | 25.9 (±2.1) | 45.3 (±3.7) |

[a]L3.6pl cells were incubated with 250 μM AG for 24 h prior to drug addition.
[b]Cells were incubated for 48 h at 37° C. with the respective conjugate.
[c]MTD of the respective conjugate.
[d]% cell migration was determined with ImageJ software[47] by determining the area not occupied by cells (white space upon microscopic examination: WS) and calculated by [((WS at 48 hr) − (WS at 0 h))/WS at 0 h] × 100%.
[e]% cell inhibition was calculated by [1 − (% cell migration at 48 h)/(% cell migration at 0 h)] × 100%. The untreated control cells migrated into 48% of the t = 0 wound space
[f]The microscope was equipped with a computer controlled x,y,z pneumatic stage (Zeiss Stemi Microscope) which allowed for reproducible imaging of each well over time.
[g]All experiments were run in triplicate and averaged to provide the data above.

When the 3,3-triamine containing systems 44a, 46a, and 47a were compared at 0.6 μM, it was seen that as the N' amine center was moved away from the macrocylic ring (44a→46a→47a), an increase in cell migration inhibition was observed. Compound 47a ($MotuCH_2$33) had the highest inhibition observed in the series. The corresponding 4,4-triamine series at 0.6 μM showed a dramatic increase in anti-migration ability upon moving the polyamine outside the ring (44b→46b→47b). This finding was especially interesting for compounds 47a and 47b, which both showed MTDs that were much higher than 0.6 μM (>130-fold and >60 fold respectively). In this regard these compounds are much less toxic than the parent 44a. This large therapeutic window makes these compounds ideal candidates to pursue in further studies in vivo. All compounds tested in this assay also demonstrated a dose-dependent response. However, dramatic increases in cell migration inhibition were not observed for higher doses, suggesting that the target of these compounds may be easily saturated.

The significant difference in cytotoxicity between 47a and 47b suggested that the polyamine tail, especially norspermidine, provides a way to modulate the cytotoxicity of future analogues. From a synthetic standpoint, this finding is advantageous as the Boc-protected norspermidine tail can be produced in fewer steps than its homospermidine counterpart.

Figure 2:
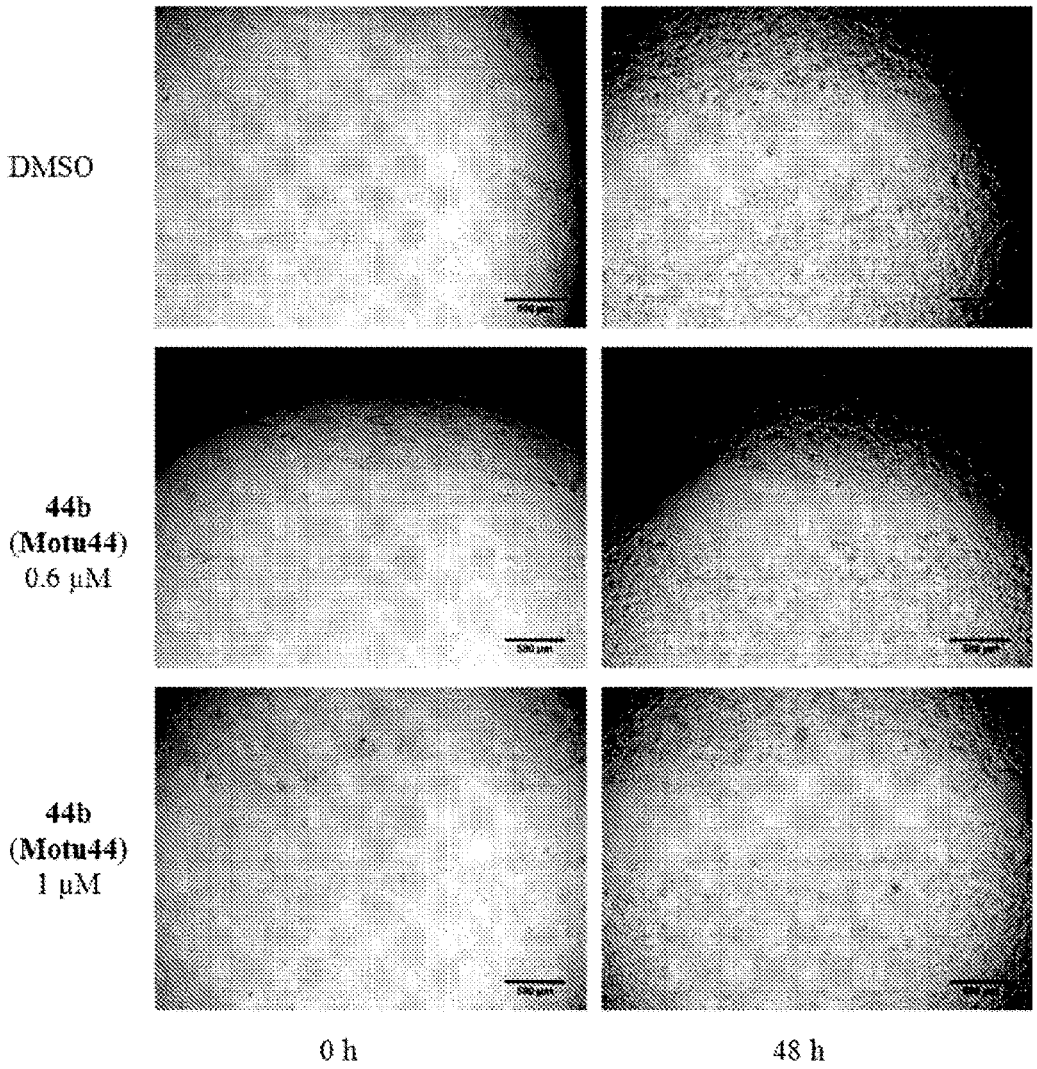
FIG. 2 shows L3.6p1 Cell Migration with 44b (Motu44) via Wound Healing Assay[a,b,]
[a]L3.6p1 cells were incubated with 250 μM AG for 24 h prior to drug addition. [b]Cells were incubated for 48 h at 37° C. with the respective conjugate.
Figure 3:
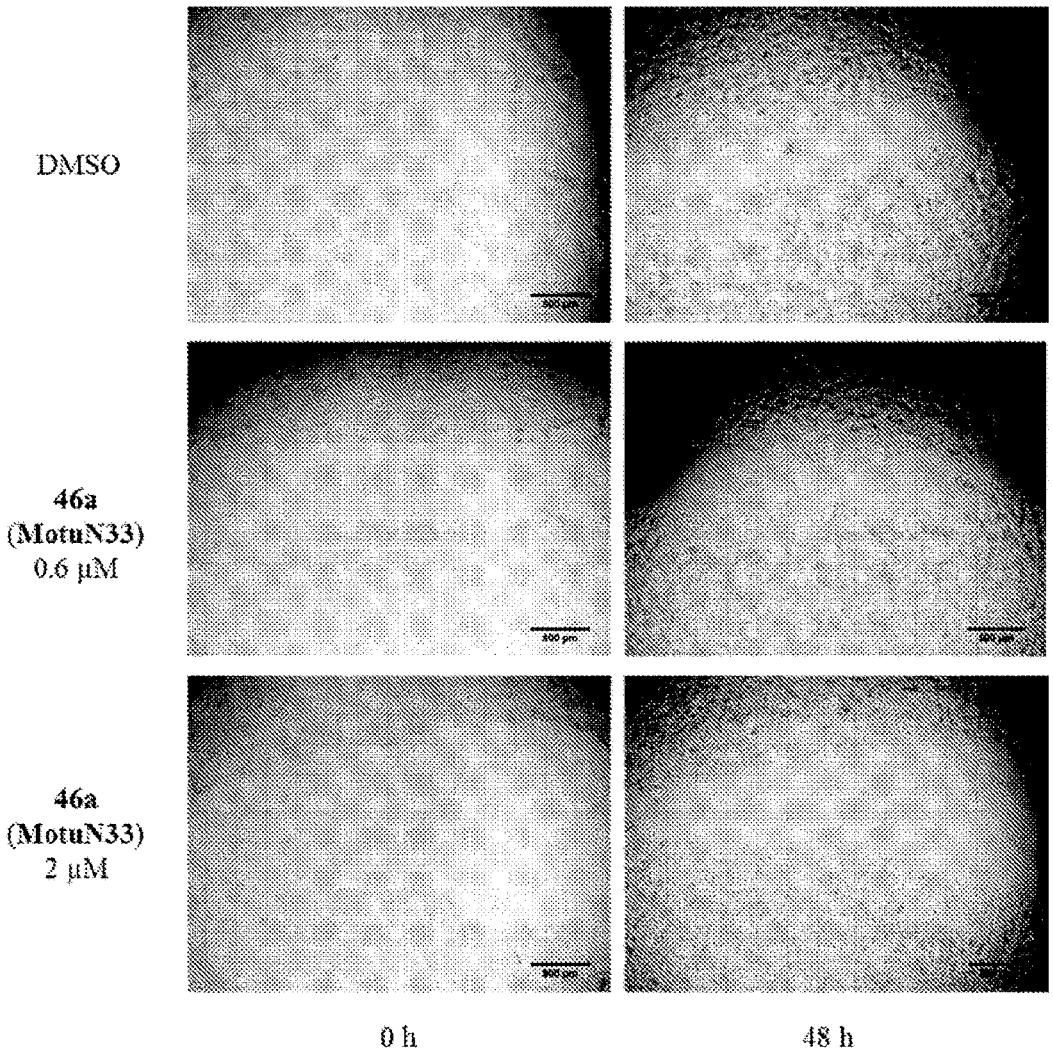
FIG. 3 shows L3.6p1 Cell Migration with 46a (MotuN33) via Wound Healing Assay[a,b]
[a]L3.6p1 cells were incubated with 250 μM AG for 24 h prior to drug addition. [b]Cells were incubated for 48 h at 37° C. with the respective conjugate.
Figure 4:
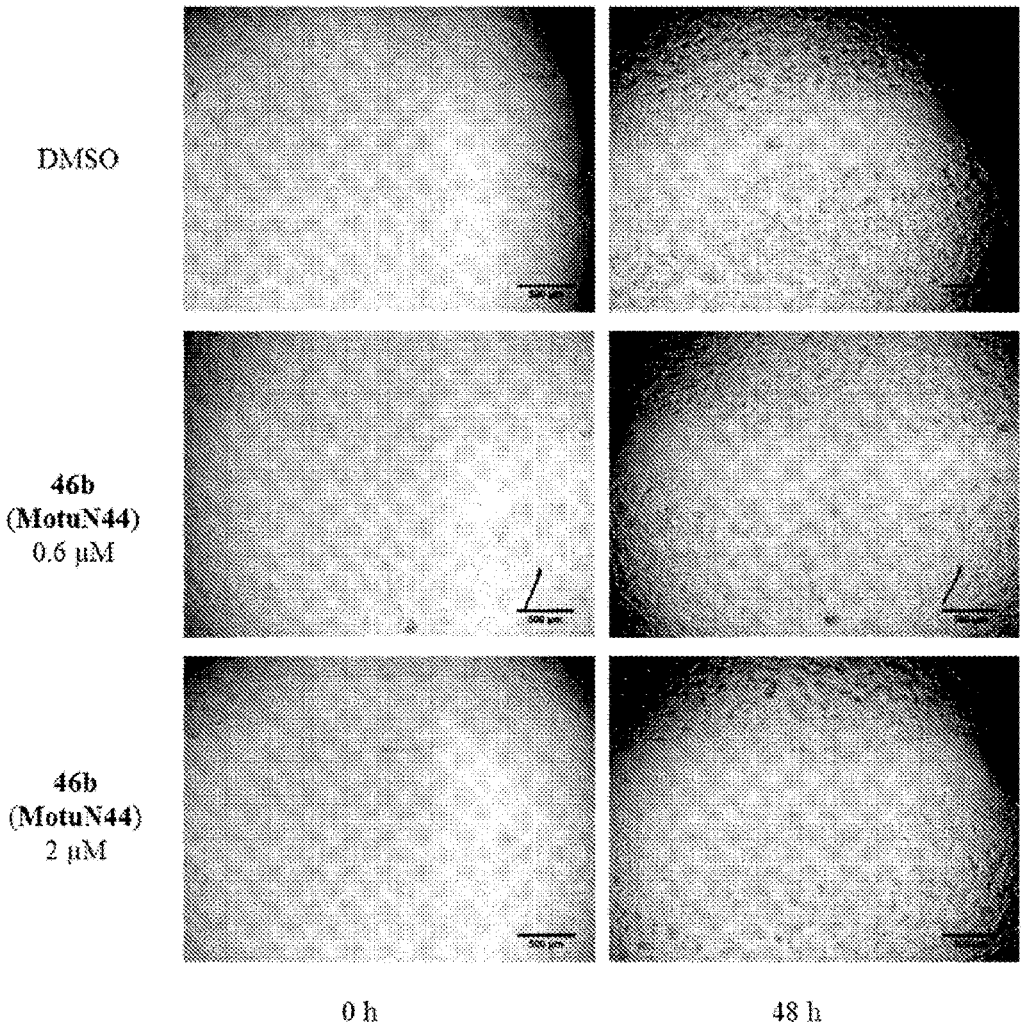
FIG. 4 shows L3.6p1 Cell Migration with 46b (MotuN44) via Wound Healing Assay[a,b]
[a]L3.6p1 cells were incubated with 250 μm AG for 24 h prior to drug addition. [b]Cells were incubated for 48 h at 37° C. with the respective conjugate.
Figure 5:
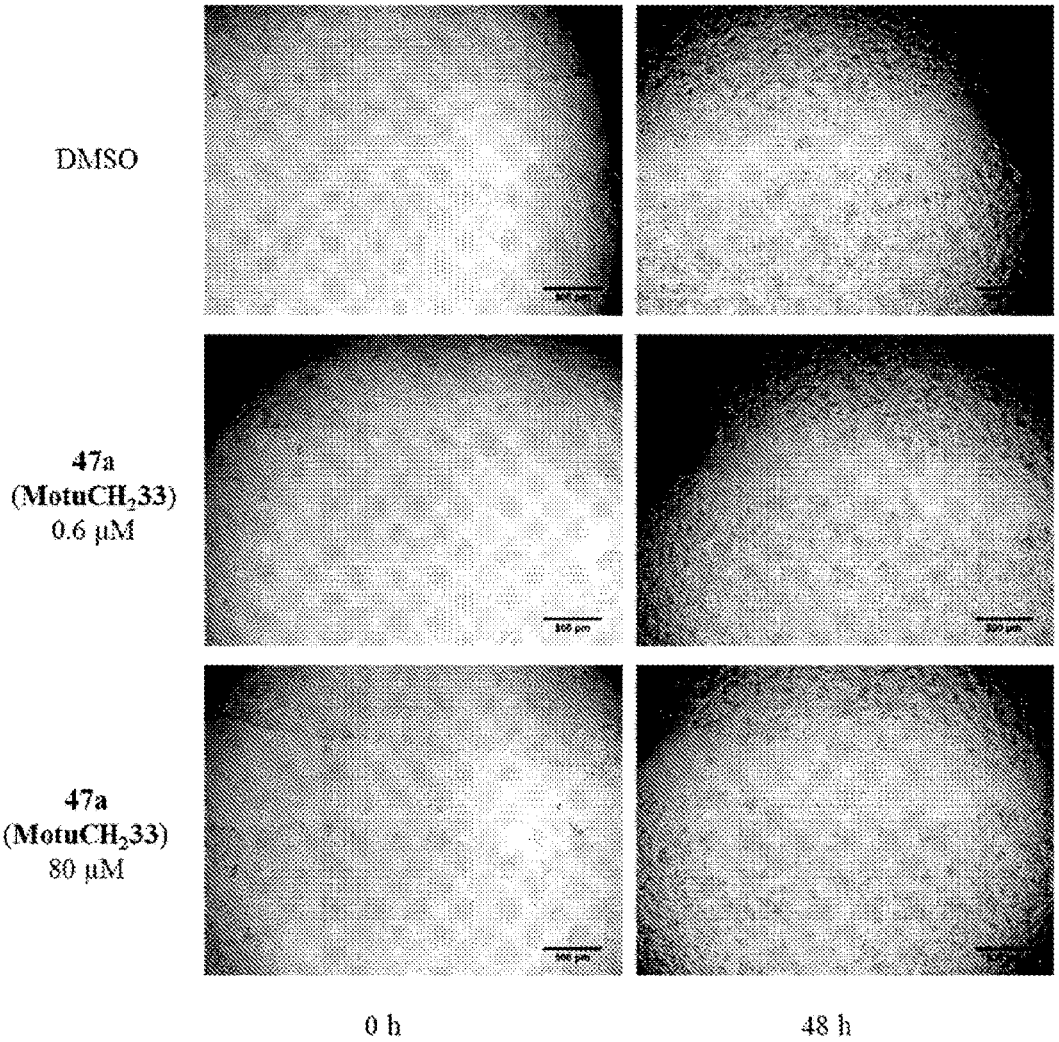
FIG. 5 shows L3.6p1 Cell Migration with 47a (Motu$CH_2$33) via Wound Healing Assay [a]L3.6p1 cells were incubated with 250 μM AG for 24 h prior to drug addition. [b]Cells were incubated for 48 h at 37° C. with the respective conjugate.
Figure 6:
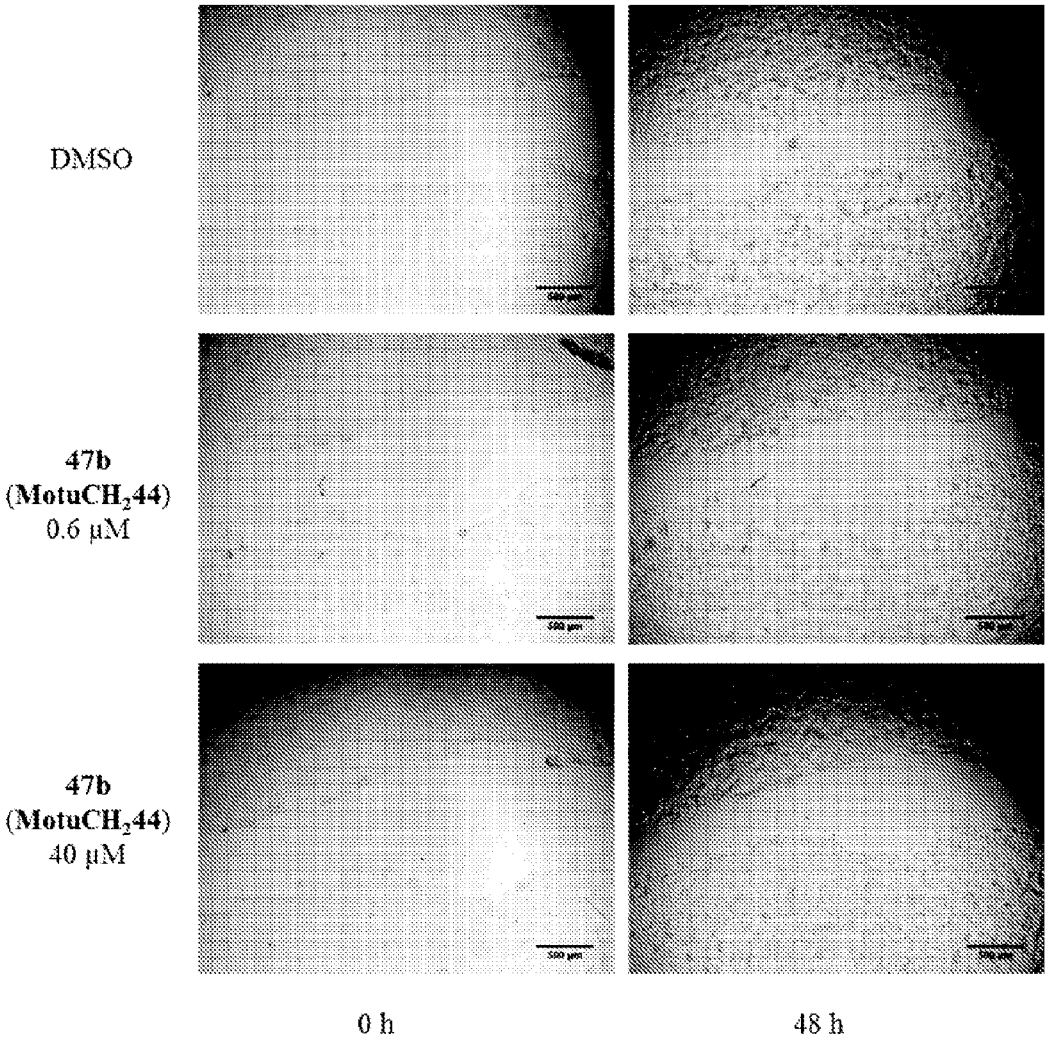
FIG. 6 shows L3.6p1 Cell Migration with 47b (Motu$CH_2$44) via Wound Healing Assay[a,b]
[a]L3.6p1 cells were incubated with 250 μM AG for 24 h prior to drug addition. [b]Cells were incubated for 48 h at 37° C. with the respective conjugate.

Taking pictures of each wound needed to be done under a 2.5× objective in order to view ~95% of each well. Unfortunately, this objective led to dark areas as seen in FIGS. 1-6. This problem was alleviated through the use of the ImageJ software.[47] This software allowed for enhancing the contrast between areas which were occupied by cells versus areas devoid of cells. In this regard, the software was able to accurately define the edges of each boundary. These capabilities then allowed for accurate area calculations which are seen in Table 3.

1.11 Summary

The $IC_{50}$/MTD determinations coupled with the wound healing assay showed that moving the polyamine message away from the macrocyclic ring had a profound effect on the biological properties of the motuporamine compounds. As stated earlier, compounds 44a-b, 46a-b, and 47a-b did not demonstrate PTS selectivity in the CHO-MG*/CHO screen. The biological evaluation in L3.6p1 showed that a carbon spacer between the $N^1$-amine and the macrocylic ring (i.e. 47a and 47b) dramatically reduced the cytotoxicity of this architecture in all three cell lines. It was also demonstrated that a change in polyamine tail from norspermidine to homospermidine showed a profound effect on cytotoxicity and the magnitude and specificity of this effect depended on the system investigated. For example, the norspermidine derivative 44a was more toxic than its homospermidine derivative 44b. The opposite trend was observed for 47a and 47b. The fact that 46a and 46b had nearly identical toxicities suggests that the type and location of the appended polyamine chain impacts the toxicity of this drug class.

The wound healing assay demonstrated that moving the $N^1$-amine away from the macrocyclic ring not only reduced the cytotoxicity, but also greatly increased the anti-migration properties. When 47a (MTD: 80 μM) and 47b (MTD: 40 μM) were both dosed at the MTD of 44a (0.6 μM), a dramatic increase in anti-migration ability was seen for 47a and 47b relative to the parent system, 44a. This large therapeutic window suggests that 47a and 47b are promising drug candidates for inhibiting the migration of aggressive metastatic cancers. These new leads are relatively non-toxic and are twice as potent as the parent 44a.

According to preliminary data (not shown), it was found that treatment of a mouse pancreatic tumor model with either compounds 47a and 44a showed dramatic decreases in tumor volume size over untreated control. Thus, this represents an exciting unexpected discovery that not only can compounds of the present invention reduce metastasis, they reduce the tumor itself.

The present disclosure provides significant advantages synthetically as compounds provided herein may be made in fewer steps from commercially available ketones instead of via the lengthy synthesis of the motuporamine heterocycle. (see Kaur, N.; Delcros, J.-G.; Martin, B.; Phanstiel, O., Synthesis and biological evaluation of dihydromotuporamine derivatives in cells containing active polyamine transporters. Journal of Medicinal Chemistry 2005, 48, 3832-3839)

1.12 Experimental 1.12.1 Materials:

Silica gel (32-63 μm) and chemical reagents were purchased from commercial sources and used without further purification. All solvents were distilled prior to use. All reactions were carried out under an $N_2$ atmosphere. $^1H$ and $^{13}C$ spectra were recorded at 400 or 75 MHz, respectively. TLC solvent systems were listed as volume percents, and $NH_4OH$ referred to concentrated aqueous $NH_4OH$. All tested compounds provided satisfactory elemental analyses.

1.12.2 Biological Studies

CHO and CHO-MG* cells were grown in RPMI 1640 medium supplemented with 10% fetal calf serum and 1% penicillin/streptomycin. Note: the media must contain L-proline (2 μg/mL) for proper growth of the CHO-MG* cells. L3.6p1 cells were grown in RPMI 1640 medium supplemented with 10% FBS and 1% penicillin/streptomycin. All cells were grown at 37° C. under a humidified 5% $CO_2$ atmosphere Aminoguanidine (1 mM for CHO and CHO-MG*, and 250 μM for L3.6p1) was added to the growth medium to prevent oxidation of the drugs by the enzyme (bovine serum amine oxidase) present in calf serum. Cells in early to mid-log phase growth were used.

1.12.3 $IC_{50}$ Determinations

Cell growth was assayed in sterile 96-well microtiter plates (Costar 3599, Corning, N.Y., USA). CHO and CHO-MG* cells were plated at 10,000 cells/mL. L3.6p1 cells were plated at 5,000 cells/mL. Drug solutions (10 μL per well) of appropriate concentration were added after an overnight incubation for each CHO cell line (90 μL of cell suspension). After exposure to the drug for 48 h, cell growth was determined by measuring formazan formation from 3-(4,5-dimethylthiazol-2-yl)-5-(3-carboxymethoxyphenyl)-2-(4-sulphenyl)-2H-tetrazolium, inner salt (MTS) using a SynergyMx BioTek microplate reader for absorbance (490 nM) measurements.[23] A 4 h incubation period was used for the MTS assay in accordance with the manufacturer's protocol.[23]

1.12.4 Wound Healing Assay

Anti-migratory properties were assayed in 96-well microtiter plates (Costar 3599, Corning, N.Y., USA). A stock suspension of L3.6p1 cells ($5.5\times10^5$ cells/mL) was prepared. L3.6p1 cells (90 μL of stock/well) were plated and allowed to grow to a confluent monolayer (48 h). Each well was then scraped with a 1 μL sterile pipet tip, photographed with a Zeiss Stemi Microscope (2.5× objective) (time=0), and then allowed to incubate for an additional 48 h period (time=48 h). Over this 48 h period, the untreated control migrated to fill 50% of the original wound. At time zero, the respective drug solutions (10 μL) were added and cell migration monitored after 48 h incubation at 37° C. with 5% $CO_2$. After drug exposure for 48 h, respective time=48 h photographs were taken by the Zeiss Stemi Microscope. These pictures (time=0 and time=48 h) were then compared and analyzed through the use of ImageJ software[47] by calculating the average area invaded by L3.6p1 cells. The results are tabulated in Table 3.

1.13 Synthetic Procedures and Characterization tert-Butyl (3-((tert-butoxycarbonyl)amino)propyl)(3-(cyclopentadecylamino)-propyl)-carbamate (50a)

A solution of diBoc-norspermidine 49a (410 mg, 1.2 mmol) in $CH_2Cl_2$ (10 mL) was added dropwise to a solution of cyclopentadecanone 48 (250 mg, 1.1 mmol) in $CH_2Cl_2$ (10 mL) and allowed to stir at room temperature for 10 minutes. Sodium triacetoxyborohydride (1.2 g, 5.6 mmol) and acetic acid (67 mg, 1.1 mmol) were then added to the solution and allowed to stir at room temperature overnight. Once the reaction was complete by $^1H$ NMR, the solution was then washed with aq. $Na_2CO_3$, and the organic layer was separated, dried over anhydrous $Na_2SO_4$, filtered, and concentrated in vacuo. After column chromatography (($R_f$=0.28 (70% hexanes/24% $CHCl_3$/5.9% EtOH/0.1% $NH_4OH$)), 50a was isolated as a pale yellow oil (450 mg, 75%). $^1H$ NMR ($CDCl_3$) δ 3.25 (t, 4H), 3.10 (t, 2H), 2.62 (m, 3H), 1.67 (m, 4H), 1.47-1.26 (m, 46H); $^{13}C$ NMR ($CDCl_3$) δ 156.0, 80.3, 79.2, 57.4, 56.9, 44.2, 43.7, 37.7, 36.7, 32.6, 31.7, 28.9, 28.5, 28.3, 27.5, 26.9, 26.8, 26.6, 26.5, 23.5. HRMS (FAB) m/z calc for $C_{31}H_{61}N_3O_4$ $(M)^{30}$ 540.4662. found 540.4734. Elemental Analysis:

$C_{31}H_{61}N_3O_4$.0.05 $H_2O$ theory C, 68.35; H, 11.31; N, 7.71. found C, 68.42; H, 11.24; N, 7.86.

tert-Butyl (4-((tert-butoxycarbonyl)amino)butyl)(4-(cyclopentadecylamino)-butyl)-carbamate (50b)

(1.54 g, 54%). $^1$H ($CDCl_3$) δ 3.18 (t, 6H), 2.59 (t, 2H), 2.52 (m, 1H), 1.55 (m, 4H), 1.51-1.22 (m, 46H); $^{13}$C NMR ($CDCl_3$) δ 156.0, 155.5, 79.1, 77.3, 56.8, 47.1, 46.5, 40.2, 32.7, 28.5, 28.4, 27.7, 27.5, 27.4, 26.8, 26.6, 26.5, 26.2, 25.9, 25.5, 23.6. HRMS (FAB) m/z calc for $C_{33}H_{65}N_3O_4$ $(M)^+$ 568.4975. found 568.5048. Elemental Analysis: $C_{33}H_{65}N_3O_4$ theory C, 69.80; H, 11.54; N, 7.40. found C, 69.58; H, 11.64; N, 7.31.

N(3-Aminopropyl)-N3-cyclopentadecylpropane-1,3-diamine (46a)

Compound 50a (450 mg, 0.8 mmol) was first dissolved in EtOH (60 mL) and stirred at 0° C. for 10 min A 4 M HCl solution (35 mL, 140 mmol) was then added dropwise and stirred for 30 min at 0° C. under $N_2$. The reaction was then slowly warmed to room temperature and stirred under $N_2$ for 4 h. Upon completion, the solvent was removed in vacuo to give 46a as a white solid (365 mg, 98%)$^1$H NMR ($D_2O$) δ 3.25 (m, 1H), 3.15 (t, 6H), 3.10 (t, 2H), 2.09 (m, 4H), 1.72 (m, 4H), 1.39-1.35 (m, 26H); $^{13}$C ($D_2O$) δ. HRMS (FAB) m/z calc for $C_{21}H_{45}N_3$ $(M+H)^+$ 340.3613. found 340.3693. Elemental Analysis: $C_{21}H_{48}Cl_3N_3$.0.05 $H_2O$ theory C, 55.57; H, 10.68; N, 9.26. found C, 55.77; H, 10.65; N, 8.98.

$N^1$-(4-Aminobutyl)-$N^4$-cyclopentadecylbutane-1,4-diamine (46b)

(1.53 g, 99%). $^1$H NMR ($D_2O$) δ 3.22 (m, 1H), 3.11 (t, 6H), 3.04 (t, 4H), 1.76-1.71 (m, 12H) 1.46-1.28 (m, 26H)$^{13}$C NMR ($D_2O$) δ 60.8, 60.5, 49.4, 46.9, 41.3, 31.4, 29.2, 28.9, 28.8, 28.6, 28.5, 26.4, 25.5, 25.1. HRMS (FAB) m/z calc for $C_{23}H_{49}N_3$ $(M+H)^+$ 368.3926. found 368.3983. Elemental Analysis: $C_{23}H_{52}Cl_3N_3$.0.05 $H_2O$ theory C, 57.32; H, 10.90; N, 8.72. found C, 57.31; H, 10.95; N, 8.52.

Methylenecyclopentadecane (51)

To a solution of methyltriphenylphosphonium iodide (12 g, 30 mmol) in THF (200 mL) was added dropwise n-BuLi (18.5 mL, 30 mmol) at 0° C. The suspension was stirred at 0° C. until a yellow color persisted, and then cyclopentadecanone, 48, (2.21 g, 9.8 mmol) was added as a solution in THF (20 mL). The mixture was allowed to warm to room temperature and stirred overnight. Upon completion, $H_2O$ was added to quench any remaining n-BuLi and any precipitates were filtered off. The filtrate was concentrated in vacuo and the residue was redissolved in $CH_2Cl_2$, washed three times with deionized $H_2O$. The organic layer was separated, dried over anhydrous $Na_2SO_4$, filtered, and then concentrated under reduced pressure to give a pale red oil. After column chromatography ($R_f$=0.9, 10% $CH_2Cl_2$/90% hexanes) 51 was isolated as a pale yellow oil (1.5 g, 69%). $^1$H NMR ($CDCl_3$) δ 4.65 (s, 2H), 1.96 (t, 4H), 1.37 (m, 4H), 1.27-1.25 (m, 20H).[48]

Cyclopentadecylmethanol (52)

A solution of the starting alkene 51 (1.5 g, 6.7 mmol) in THF (8 mL) was added dropwise to a cooled 1 M solution of $BH_3$-THF (20.2 mL, 20.2 mmol). The reaction was stirred at 0° C. for 1 h and then allowed to stir for 2 h at room temperature. Excess diborane was decomposed by dropwise addition of water (10 mL). A 3 M solution of NaOH (10 mL) was then added, followed by dropwise addition of 30% $H_2O_2$ (10 mL). The reaction was stirred for 1 h at room temperature and $K_2CO_3$ (100 mg) was then added. The layers were then separated and the aqueous layer was extracted three times with $CH_2Cl_2$, the organic layers were pooled, dried over $Na_2SO_4$, then filtered and concentrated. After column chromatography ($R_f$=0.31, 50% hexanes/50% $CH_2Cl_2$) 52 was isolated as a yellow oil (1.2 g, 74%). $^1$H NMR ($CDCl_3$) δ 3.49 (t, 2H), 1.53 (m, 1H), 1.41-1.22 (m, 28H); $^{13}$C NMR ($CDCl_3$) δ 67.0, 39.5, 29.6, 27.5, 27.0, 26.7, 26.6, 26.5, 25.0.

Cyclopentadecanecarbaldehyde (53)

To a solution of alcohol 52 (300 mg, 1.25 mmol) in $CH_2Cl_2$ (20 mL) was added PCC (404 mg, 1.87 mmol) at room temperature. The reaction was monitored by TLC (50% hexanes/50% $CH_2Cl_2$) until complete (60 min) Upon reaching completion, the mixture was then diluted with $Et_2O$, filtered through Celite and concentrated in vacuo to give aldehyde 53 as a yellow oil that was used without further purification (250 mg crude). $^1$H NMR ($CDCl_3$) δ 9.61 (s, 1H), 2.43 (m, 2H), 2.29 (m, 1H), 1.62 (m, 4H),1.49 (m, 4H), 1.44-1.31 (m, 20H). This aldehyde was found to be unstable and was best used immediately in subsequent steps.

tert-Butyl (3-((tert-butoxycarbonyl)amino)propyl)(3-((cyclopentadecylmethyl)amino)-propyl)carbamate (54a)

A solution of diBoc-norspermidine 49a (496 mg, 1.5 mmol) in $CH_2Cl_2$ (12 mL) was added dropwise to a solution of the crude cyclopentadecanecarbaldehyde 53 (310 mg crude) in $CH_2Cl_2$ (12 mL) and allowed to stir at room temperature for 10 min Acetic acid (72 pt, 1.26 mmol) was then added and the solution was stirred for 20 min, followed by the addition of sodium triacetoxyborohydride (1.33 g, 6.3 mmol) and stirred at room temperature overnight. Upon completion, the reaction mixture was washed three times with aq. 10% $Na_2CO_3$, the organic layer was separated, dried over anhydrous $Na_2SO_4$, filtered and concentrated in vacuo. After column chromatography ($R_f$=0.25; 94.5% $CH_2Cl_2$/5% MeOH/0.5% $NH_4OH$), 54a was isolated as a pale yellow oil (250 mg, 36% over 2 steps). $^1$H NMR ($CDCl_3$) δ 3.24 (t, 4H), 3.11 (t, 2H), 2.73 (d, 2H), 2.62 (m, 4H), 2.48 (t, 2H), 1.92 (m, 1H), 1.70 (m, 4H), 1.48-1.26 (m, 46H); $^{13}$C NMR ($CDCl_3$) δ 156.1, 80.1, 79.5, 79.2, 54.6, 54.0, 46.2, 46.1, 44.2, 43.7, 37.4, 36.1, 30.6, 29.0, 28.7, 28.4, 28.2, 27.6, 27.1, 26.9, 26.8, 26.6, 26.5, 24.7, 24.5. HRMS (FAB) m/z calc for $C_{32}H_{63}N_3O_4$ $(M+H)^+$ 554.4819. found 554.4894. Elemental Analysis: $C_{32}H_{63}N_3O_4$.0.05 $H_2O$ theory C, 68.79; H, 11.38; N, 7.52. found C, 68.74; H, 11.30; N, 7.27.

tert-Butyl (4-((tert-butoxycarbonyl)amino)butyl)(4-((cyclopentadecylmethyl)amino)-butyl)carbamate (54b)

Compound 54b was synthesized using a similar procedure as 54a. (100 mg, 45% over 2 steps). $^1$H NMR ($CDCl_3$) δ 3.15 (t, 6H), 2.60 (t, 2H), 2.47 (d, 2H), 1.52 (m, 9H), 1.51-1.42 (s, 18H), 1.39-1.23 (m, 28H); $^{13}$C NMR ($CDCl_3$) δ 156.0, 156.6, 79.2, 54.8, 49.8, 46.9, 46.7, 40.3, 36.9, 31.0, 28.5, 28.4, 27.6, 27.4, 27.0, 26.8, 26.7, 26.5, 24.8. HRMS (FAB)

m/z calc for $C_{34}H_{67}N_3O_4$ $(M+H)^+$ 582.5132. found 582.5213. Elemental Analysis: $C_{34}H_{67}N_3O_4.0.05\ H_2O$ theory C, 69.59; H, 11.53; N, 7.16. found C, 69.59; H, 11.24; N, 7.22.

$N^1$-(3-aminopropyl)-$N^3$-(cyclopentadecylmethyl) propane-1,3-diamine (47a)

Compound 54a (250 mg, 0.5 mmol) was first dissolved in EtOH (35 mL) and stirred at 0° C. for 10 min A 4 M HCl solution (17 mL, 68 mmol) was then added dropwise and stirred for 30 min at 0° C. under $N_2$. The reaction was then slowly warmed to room temperature and stirred under $N_2$ for 4 h. Upon completion, the solvent was removed in vacuo to give 46a as a white solid (191 mg, 93%) $^1$H NMR ($D_2O$) δ 3.16 (t, 4H), 3.09 (t, 4H), 2.93 (d, 2H), 2.10 (m, 4H), 1.82 (m, 1H), 1.32 (m, 30H); $^{13}$C NMR ($D_2O$) δ 54.7, 47.3, 46.9, 38.7, 36.5, 31.6, 29.2, 28.8, 28.7, 28.6, 28.4, 26.0, 25.8, 24.8. HRMS (FAB) m/z calc for $C_{22}H_{47}N_3$ $(M+H)^+$ 354.3770. found 354.3846. Elemental Analysis: $C_{22}H_{50}N_3Cl_3.0.15\ H_2O$ theory C, 55.32; H, 10.61; N, 8.80. found C, 55.59; H, 10.85; N, 8.47.

$N^1$-(4-aminobutyl)-$N^4$-(cyclopentadecylmethyl)butane-1,4-diamine (47b)

Compound 47b was generated using a procedure similar to that described for 47a. (80 mg, 95%). $^1$H NMR ($D_2O$) δ 3.07 (t, 4H), 3.04 (t, 4H), 2.93 (d, 2H), 1.76 (m, 9H), 1.33 (m, 28H); $^{13}$C NMR ($D_2O$) δ 54.6, 49.8, 49.3, 41.2, 36.5, 31.8, 29.3, 29.9, 29.8, 28.7, 28.5, 26.3, 26.0, 25.3, 25.2, 25.0. HRMS (FAB) m/z calc for $C_{24}H_{51}N_3$ $(M+H)^+$ 382.4083. found 382.4159. Elemental Analysis: $C_{24}H_{54}N_3Cl_3.0.2\ H_2O$ theory C, 56.45; H, 10.74; N, 8.23. found C, 56.48; H, 10.78; N, 8.29.

1.14 References

All references set forth herein in this document are incorporated by reference herein to the extent that the subject matter therein does not conflict with the existing disclosure.

1. (a) Cullis, P. M.; Green, R. E.; Merson-Davies, L.; Travis, N., Probing the mechanism of transport and compartmentalization of polyamines in mammalian cells. Chem. Biol. 1999, 6, 717-729; (b) Seiler, N.; Delcros, J.-G.; Moulinoux, J. P., Polyamine transport in mammalian cells. An update. Int. J. Biochem. 1996, 28, 843-861; (c) Seiler, N.; Dezeure, F., Polyamine transport in mammalian cells Int. J. Biochem. 1990, 22, 211-218.
2. (a) Phanstiel, O.; Price, H. L.; Wang, L.; Juusola, J.; Kline, M.; Shah, S. M., The effect of polyamine homologation on the transport and cytotoxicity properties of polyamine-(DNA intercalator) conjugates. The Journal of Organic Chemistry 2000, 65, 5590-5599; (b) Wang, L.; Price, H. L.; Juusola, J.; Kline, M.; Phanstiel, O. I., Influence of polyamine architecture on the transport and topoisomerase II inhibitory properties of polyamine DNA-intercalator conjugates. Journal of Medicinal Chemistry 2001, 44, 3682-3691; (c) Wang, C.; Delcros, J.-G.; Biggerstaff, J.; Phanstiel, O., Synthesis and biological evaluation of N1-(anthracen-9-ylmethyl)triamines as molecular recognition elements for the polyamine transporter. Journal of Medicinal Chemistry 2003, 46, 2663-2671; (d) Wang, C.; Delcros, J.-G.; Biggerstaff, J.; Phanstiel, O., Molecular requirements for targeting the polyamine transport system: Synthesis and biological evaluation of polyamine anthracene conjugates. Journal of Medicinal Chemistry 2003, 46, 2672-2682; (e) Wang, C.; Delcros, J.-G.; Cannon, L.; Konate, F.; Carias, H.; Biggerstaff, J.; Gardner, R. A.; Phanstiel, O., Defining the molecular requirements for the selective delivery of polyamine conjugates into cells containing active polyamine transporters. Journal of Medicinal Chemistry 2003, 46, 5129-5138; (f) Kaur, N.; Delcros, J.-G.; Martin, B.; Phanstiel, O., Synthesis and biological evaluation of dihydromotuporamine derivatives in cells containing active polyamine transporters. Journal of Medicinal Chemistry 2005, 48, 3832-3839; (g) Gardner, R. A.; Delcros, J.-G.; Konate, F.; Breitbeil, F.; Martin, B.; Sigman, M.; Phanstiel, O., N1-Substituent effects in the selective delivery of polyamine-conjugates into cells containing active polyamine transporters. Journal of Medicinal Chemistry 2004, 47, 6055-6069.
3. Palmer, A. J. W., H. M., The polyamine transport system as a target for anticancer drug development. Amino Acids 2010, 38, 415-422.
4. (a) Soulet, D. G., B.; Rivest, S.; Audette, M.; Poulin, R., A fluorescent probe of polyamine transport accumulates into intracellular acidic vesicles via a two-step mechanism. The Journal of Biological Chemistry 2004, 279, 49355-49366; (b) Soulet, D. C., L.; Kaouass, M.; Charest-Gaudreault, R.; Audette, M.; Poulin, R., Role of endocytosis in the internalization of spermidine-C(2)-BODIPY, a highly fluorescent probe of polyamine transport. Biochem. J. 2002, 367, 347-357.
5. (a) Belting, M.; Persson, S.; Fransson, L.-A., Proteoglycan involvement in polyamine uptake. Biochem. J. 1999, 338, 317-323; (b) Belting, M. M., K.; Jonsson, M.; Cheng, F.; Sandgren, S.; Jonsson, S.; Ding, K.; Delcros, J-G.; Fransson, L-A., Glypican-1 is a vehicle for polyamine uptake in mammalian cells: A pivotal role for nirosothiol-derived nitric oxide. The Journal of Biological Chemistry 2003, 278, 47181-47189.
6. Delcros, J.-G. T., S.; Carrington, S.; Martin, B.; Renault, J.; Blagbrough, I. S.; Uriac, P., Effect of spermine conjugation on the cytotoxicity and cellular transport of acridine. Journal of Medicinal Chemistry 2002, 45, 5098-5111.
7. (a) Heaton, M.A. F., Wayne F., Methylglyoxal-bis(guanylhydrazone)-Resistant Chinese Hamster Ovary Cells: Genetic Evidence That More Than A Single Locus Controls Uptake. Journal of Cellular Physiology 1988, 136, 133-139; (b) Mandel, J. L.; Flintoff, W. F., Isolation of mutant mammalian cells altered in polyamine transport. J. Cell. Physiol. 1978, 97, 335-344.
8. Bergeron, R. J.; McManis, J. S.; Weimar, W. R.; Schreier, K.; Gao, F.; Wu, Q.; Ortiz-Ocasio, J.; Luchetta, G.; Porter, C.; Vinson, J. R., The role of charge in polyamine analogue recognition. Journal of Medicinal Chemistry 1995, 38, 2278-2285.
9. Phanstiel, O. I.; Kaur, N.; Delcros, J.-G., Structure-activity investigations of polyamine-anthracene conjugates and their uptake via the polyamine transporter. Amino Acids 2007, 33, 305-313.
10. (a) Bergeron, R. J.; Feng, Y.; Weimar, W. R.; McManis, J. S.; Dimova, H.; Porter, C. W.; Raisler, B.; Phanstiel, O., A comparison of structure-activity relationships between spermidine and spermine analogue antineoplastics. Journal of Medicinal Chemistry 1997, 40, 1475-1494; (b) Kramer, D. L.; Miller, J. T.; Bergeron, R. J.; Khomutov, R.; Khomutov, A.; Porter, C. W., Regulation of polyamine transport by polyamines and polyamine analogues. J. Cell. Physiol. 1993, 155, 399-407; (c) Byers, T. L.;

Wechter, R.; Nuttall, M. E.; Pegg, A. E., Expression of a human gene for polyamine transport in chinese hamster ovary cells. Biochem. J. 1989, 263, 745-752.

11. Kaur, N.; Delcros, J.-G.; Imran, J.; Khaled, A.; Chehtane, M.; Tschammer, N.; Martin, B.; Phanstiel, O. IV, A comparison of chloroambucil- and xylene-containing polyamines leads to improved ligands for accessing the polyamine transport system. Journal of Medicinal Chemistry 2008, 51, 1393-1401.

12. (a) Gahl, W.A.; Pitot, H. C., Reversal by aminoguanidine of the inhibition of proliferation of human fibroblasts by spermidine and spermine Chem.-Biol. Interact. 1978, 22, 91-98; (b) Morgan, D. M., Polyamine oxidases and oxidized polyamines. In Physiology of Polyamines, Bachrach, U.; Heimer,Y. M., Eds. CRC Press: Boca Raton, Fla., 1989; Vol. 1, pp 203-229.

13. (a) Casero, R. A.; Celano, P.; Ervin, S. J.; Wiest, L.; Pegg, A. E., High specific induction of spermidine/spermine N1-acetyltransferase in a human large cell lung carcinoma. Biochem. J. 1990, 270, 615-620; (b) Fogel-Petrovic, M.; Kramer, D. L.; Vujcic, S.; Miller, J.; McManis, J. S.; Bergeron, R. J.; Porter, C. W., Structural basis for differential induction of spermidine/spermine $N^1$-Acetyltransferase activity by novel spermine analogs. Molecular Pharmacology 1997, 52, 69-74; (c) Coleman, C. S.; Pegg, A. E., Polyamine analogues inhibit the ubiquitination of spermidine/spermine N1-acetyltransferase and prevent its targeting to the proteasome for degradation. Biochem. J. 2001, 358, 137-145; (d) Kramer, D. L.; Fogel-Petrovic, M.; Diegelman, P.; Cooley, J. M.; Bemacki, R. J.; McManis, J. S.; Bergeron, R. J.; Porter, C. W., Effects of novel spermine analogues on cell cycle progression and apoptosis in MALME-3M human melanoma cells. Cancer Research 1997, 57, 5521-5527; (e) Barreiro, E. J.; Kummerle, A. E.; Fraga, C. A. M., The methylation effect in medicinal chemistry. Chemical Reviews 2011.

14. Kaur, N.; Delcros, J.-G.; Archer, J.; Weagraff, N. Z.; Martin, B.; Phanstiel, O. I., Designing the polyamine pharmacophore: Influence of N-substituents on the transport behavior of polyamine conjugates. Journal of Medicinal Chemistry 2008, 51, 2551-2560.

15. (a) Flescher, E. B., T. L.; Ballester, A.; Houk, R.; Talal, N., Increased polyamines may downregulate interleukin 2 production in rheumatoid arthritis. J. Clin. Invest. 1989, 83, 1356-1362; (b) Flescher, E. B., T. L.; Talal, N., Polyamine oxidation down-regulates IL-2 production by human peripheral blood mononuclear cells. The Journal of Immunology 1989, 142, 907-912; (c) Flescher, E. F., D.; Talal, N., Polyamine-dependent production of lymphocytotoxic levels of ammonia by human peripheral blood monocytes. Immunology Letters 1991, 28, 85-90; (d) Suzuki, O. M., T.; Katsumata, Y., Determination of polyamine oxidase activities in human tissues. Experientia 1984, 40, 838-839.

16. Seiler, N. D., B.; Gosse, F.; Raul, F., Spermine cytotoxicity to human colon carcinoma-derived cells (CaCo-2). Cell Biology and Toxicology 2000, 16, 117-130.

17. Kruczynski, A.; Vandenberghe, I.; Pillon, A.; Pesnel, S.; Goetsch, L.; Barret, J.-M.; Guminski, Y; Le Pape, A.; Imbert, T.; Bailly, C.; Guilbaud, N., Preclinical activity of F14512, designed to target tumors expressing an active polyamine transport system. Invest. New Drugs 2011, 29, 9-21.

18. Asaki, T.; Hamamoto, T.; Sugiyama, Y; Kuwano, K.; Kuwabara, K., Structure-activity studies on diphenylpyrazine derivatives: A novel class of prostacyclin receptor agonists. Bioorganic and Medicinal Chemistry Letters 2007, 15, 6692-6704.

19. Kane, B. E.; Grant, M. K. O.; El-Fakahany, E. E.; Ferguson, D. M., Synthesis and evaluation of xanomeline analogs-Probing the wash-resistant phenomenom at the $M_1$ muscarinic acetylcholine receptor. Bioorganic and Medicinal Chemistry Letters 2008, 16, 1376-1392.

20. Middleton, R.; Briddon, S.; Cordeaux, Y.; Yates, A.; Dale, C.; George, M.; Baker, J.; Hill, S.; Kellam, B., New fluorescent adenosine $A_1$-receptor agonists that allow quantification of ligand-receptor interactions in microdomains of single living cells. Journal of Medicinal Chemistry 2007, 50, 782-793.

21. (a) Prugh, J.; Birchenough, L.; Egberton, M., A simple method of protecting a secondary amine with tert butyloxycarbonyl (BOC) in the presence of a primary amine. Synthetic Communications 1992, 22, 2357-2360; (b) Laduron, F.; Tamborowski, V.; Moens, L.; Horvath, A.; De Smaele, D.; Leurs, S., Efficient and scalable method for the selective alkylation and acylation of secondary amines in the presence of primary amines Organic Process Research and Development 2005, 9, 102-104.

22. (a) Fogel-Petrovic, M.; Shappell, N. W.; Bergeron, R. J.; Porter, C. W., Polyamine and polyamine analog regulation of spermidine/spermine $N^1$-acetyltransferase in MALME-3M human melanoma cells. The Journal of Biological Chemistry 1993, 268, 19118-19125; (b) Kramer, D. L.; Vujcic, S.; Diegelman, P.; Alderfer, J.; Miller, J.; Black, J. D.; Bergeron, R. J.; Porter, C. W., Polyamine analogue induction of the p53-p21$^{WAF1/CIP1}$ Rb pathway and $G_1$ arrest in human melanoma cells. Cancer Research 1999, 59, 1278-1286.

23. Mosmann, T., Rapid colorimetric assay for cellular growth and survival: Application to proliferation and cytotoxic assays. J. Immunol. Methods 1983, 65, 55-63.

24. (a) Gerner, E. W. M., F. L.; Goldschmid, S.; Lance, P.; Pelot, D., Rationale for, and design of, a clinical trial targeting polyamine metabolism for colon cancer chemoprevention. Amino Acids 2007, 33, 189-195; (b) Chen, Y W., R. S.; Burns, M. R.; Boorman, D. W.; Klein-Szanto, A., Combination therapy with 2-difluoromethylornithine and a polyamine transport inhibitor against murine squamous cell carcinoma. Int. J. Cancer 2006, 118, 2344-2349.

25. (a) Wallick, C. J. G., I.; Thorne, M.; Feith, D. J.; Takasaki, K. Y; Wilson, S. M.; Seki, J. A.; Pegg, A. E.; Byus, C. V.; Bachmann, A S , Key role for p27Kip1, retinoblastoma protein Rb, and MYCN in polyamine inhibitor-induced G1 cell cycle arrest in MYCN-amplified human neuroblastoma cells. Oncogene 2005, 24, 5606-5618; (b) Hibshoosh, H. J., M.; Weinstein, I. B., Effects of overexpression of ornthine decarboxylase (ODC) on growth control and oncogene-induced cell transformation. Oncogene 1991, 6, 739-743.

26. (a) Meyskens Jr, F. L. G., E. W., Development of Difluoromethylornithine (DFMO) as a chemoprevention agent. Clinical Cancer Research 1999, 5, 945-951; (b) Fabian, C. J. K., B. F.; Brady, D. A.; Mayo, M. S.; Chang, C. H.; Ferraro, J. A.; Zalles, C. M.; Stanton, A. L.; Masood, S.; Grizzle, W. E.; Boyd, N. F.; Arneson, D. W.; Johnson, K. A., A Phase II breast cancer chemoprevention trial of oral alpha-difluoromethylornithine: Breast tissue, imaging, and serum and urine biomarkers. Clinical Cancer Research 2002, 8, 3105-3117; (c) Abeloff, M. D. S., M.; Luk, G. D.; Griffin, C. A.; Hermann, J.; Blanc, O.; Sjoerdsma, A.; Baylin, S. B., Phase I trial and pharmacokinetic studies of alpha-difluoromethylornithine an inhibitor of polyamine biosynthesis. Journal of Clinical Oncology 1984, 2, 124-130.

27. (a) Seiler, N., Thirty years of polyamine-related approaches to cancer therapy. Retrospect and prospect. Part 2. Structural analogues and derivatives. Current Drug Targets 2003, 4, 537-564; (b) Gerner, E. W. M., F. L., Polyamines and cancer: old molecules, new understanding. Nature Reviews Cancer 2004, 4, 781-792.
28. Phanstiel, O. A., J. J., Design of polyamine transport inhibitors as therapeutics. In Polyamine Drug Discovery, 1 ed.; Casero, R. W., P., Ed. Royal Society of Chemistry: 2011; p 302.
29. American Cancer Society. Cancer facts & figures 2012.
30. (a) Basu Roy, U. K. R., Nathaniel S.; Kachel, Karen L.; Gerner, Eugene W., Activated K-RAS increases polyamine uptake in human colon cancer cells through modulation of caveolar endocytosis. Molecular Carcinog. 2008, 47, 538-553; (b) Basuroy, U. K. G., E. W., Emerging concepts in targeting the polyamine metabolic pathway in epithelial cancer chemoprevention and chemotherapy. Journal of Biochemistry 2006, 139, 27-33.
31. Covassin, L. D., M.; Charest-Gaudreault, R.; Audette, M.; Bonneau, M.-J.; Poulin, R., Synthesis of spermidine and norspermidine dimers as high affinity polyamine transport inhibitors. Bioorg. Med. Chem. Lett. 1999, 9, 1709-1714.
32. Burns, M. R. C., C. Lance; Vanderwerf, Scott M.; Ziemer, Josh R.; Weeks, Reitha S.; Cai, Feng; Webb, Heather K.; Graminski, Gerard F., Amino acid/spermine conjugates: Polyamine amides as potent spermidine uptake inhibitors. Journal of Medicinal Chemistry 2001, 44, 3632-3644.
33. Burns, M. R.; Graminski, G. F.; Weeks, R. S.; Chen, Y.; O'Brien, T. G., Lipophilic lysine-spermine conjugates are potent polyamine transport inhibitors for use in combination with a polyamine biosynthesis inhibitor. Journal of Medicinal Chemistry 2009, 52, 1983-1993.
34. Gardner, R. A.; Kinkade, R.; Wang, C.; Phanstiel, O. I., Total synthesis of petrobactin and its homologues as potential growth stimuli for Marinobacter hydrocarbonclasticus, an oil-degrading bacteria. The Journal of Organic Chemistry 2004, 69, 3530-3537.
35. Azmi, A. S. A., A.; Banerjee, S.; Rangnekar, V. M.; Mohammad, R. M.; Sarkar, F. H., Chemoprevention of pancreatic cancer: Characterization of Par-4 and its modulation by 3,3' diindolylmethane (DIM). Pharmaceutical Research 2008, 25, 2117-2124.
36. Williams, D. E. L., P.; Andersen, R. J., Motuporamines A-C, cytotoxic alkaloids isolated from the marine sponge Xestospongia exigua (Kirkpatrick). Journal of Organic Chemistry 1998, 63, 4838-4841.
37. (a) Williams, D. E.; Craig, K. S.; Patrick, B.; McHardy, L. M.; van Soest, R.; Roberge, M.; Andersen, R. J., Motuporamines, anti-invasion and anti-angiogenic alkaloids from the marine sponge Xestospongia exigua (Kirtpatrick): Isolation, structure elucidation, analogue synthesis, and conformational analysis. The Journal of Organic Chemistry 2002, 67, 245-258; (b) Roskelley, C. D.; Williams, D. E.; McHardy, L. M.; Leong, K. G.; Armelle, T.; Karsan, A.; Andersen, R. J.; Dedhar, S.; Roberge, M., Inhibition of tumor cell invasion and angiogenesis by motuporamines Cancer Research 2001, 61, 6788-6794.
38. (a) Baetz, K. M., L.; Gable, K.; Tamsin, T.; Reberioux, D.; Bryan, J.; Andersen, R. J.; Dunn, T.; Hieter, Roberge, M., Yeast genome-wide drug-induced haploinsufficiency screen to determine drug mode of action. PNAS 2004, 101, 4525-4530; (b) McHardy, L. M. A study of the mechanism of action of novel inhibitors of tumour cell invasion. The University of British Columbia, Vancouver, British Columbia, 2007; (c) Kemmer, D. M., L. M.; Hoon, S.; Reberioux, D.; Giaever, G.; Nislow, C.; Roskelley, C. D.; Roberge, M., Combining chemical genomics screens in yeast to reveal spectrum of effects of chemical inhibition of sphingolipid biosynthesis. BMC Microbiology 2009, 9, 9-26.
39. Roberge, M., Defining drug targets in yeast haploinsufficiency screens: application to human translational pharmacology. Sci. Signal. 2008, 1, pt5.
40. Ellenbroek, S. C., J., RhoGTPases: functions and associations with cancer. Clin. Exp. Metastasis 2007, 24 (8), 657-672.
41. To, K. C. W. L., K. T.; Roskelley, C. D.; Andersen, R. J.; O'Connor, T. P., The anti-invasive compound motuporamine C is a robust smitulator of neuronal growth cone collapse. Neuroscience 2006, 139, 1263-1274.
42. Vial, E. S., E.; Marshall, C. J., ERK-MAPK signaling coordinately regulates activity of Racl and RhoA for tumor cell motility. Cancer Cell 2003, 4 (1), 67-79.
43. Breitbeil, F.; Kaur, N.; Delcros, J.-G.; Martin, B.; Abboud, K. A.; Phanstiel, O., Modeling the preferred shapes of polyamine transporter ligands and dihydromotuporamine-C mimics: Shovel versus hoe. Journal of Medicinal Chemistry 2006, 49, 2407-2416.
44. Goldring, W. P. D. W., Larry, Cytotoxic Alkaloids Motuporamines A-C: Synthesis and Structural Verification. Organic Letters 1999, 1 (9), 1471-1473.
45. Furstner, A.; Rumbo, A., Ring-closing alkyne metathesis. Stereoselective synthesis of the cytotoxic marine alkaloid motuporamine C. The Journal of Organic Chemistry 2000, 65, 2608-2611.
46. Shrestha, A. S., D.; Malladi, S. S.; Warshakoon, H. J.; David, S. A., Structure-activity relationships of lipopolysaccharide sequestration in N-alkylpolyamines. Bioorg. Med. Chem. Lett. 2009, 19, 2478-2481.
47. Straatman, K., Wound healing assay. In http://www.le.ac.uk/biochem/microscopy/wound-healing-assay.html, University of Leicester, U.K., 2008.
48. Welch, S. C. L., J-P., Reduction of [(phenylthio)methyl] carbinyl benzoate esters to alkenes with titanium metal. J. Org. Chem. 1981, 46, 4072-4076.

The teachings of all cited references are incorporated in their entirety to the extent they are not inconsistent with the teachings herein. U.S. Patent Pubs 20090069441, 20090155265, and 20070213397, and PCT Publication No. WO02058679 are further incorporated by reference herein for background information, as well as teachings on pharmaceutical compositions, formulations, dosages and modes of administration that can be applied to the compounds and compound combinations described herein.

What is claimed is:

1. A compound represented by the formula:

(I)

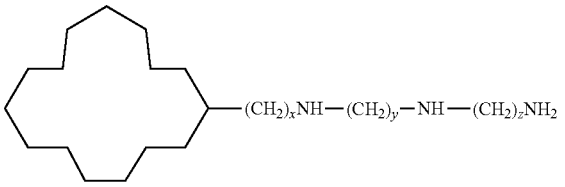

wherein x=[1-6] *0-6*;

wherein y=3 or 4 or 5;

wherein z=3 or 4 or 5;

, or a pharmaceutically acceptable salt thereof.

2. The compound of claim 1, wherein the compound comprises structure (47a)

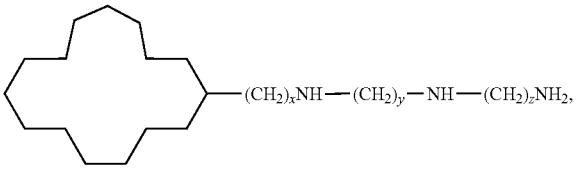

47a: x = 1, y = 3, z = 3 or a pharmaceutically acceptable salt thereof.

3. The compound of claim 1, wherein the compound comprises structure (47b)

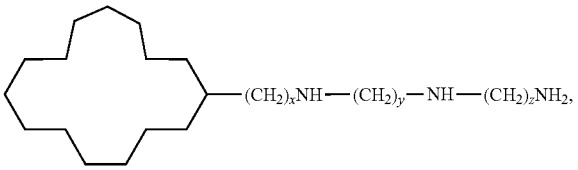

47b: x = 1, y = 4, z = 4 or a pharmaceutically acceptable salt thereof.

4. A pharmaceutical composition comprising a compound of claim 1 and a pharmaceutically acceptable carrier.

5. The pharmaceutical composition of claim 4, wherein the compound comprises compound (47a),

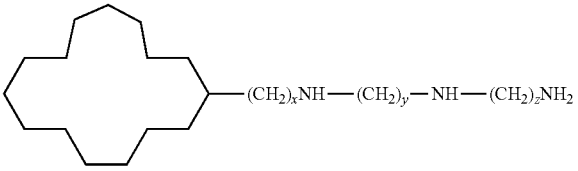

47a: x = 1, y = 3, z = 3 or a pharmaceutically acceptable salt thereof; or compound

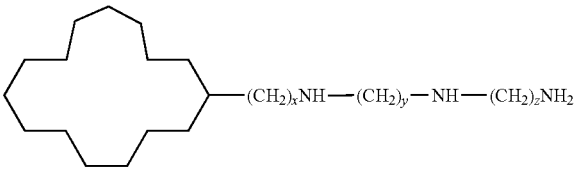

47b: x = 1, y = 4, z = 4

(47b), or a pharmaceutically acceptable salt thereof.

6. A compound represented by the formula:

(IV)

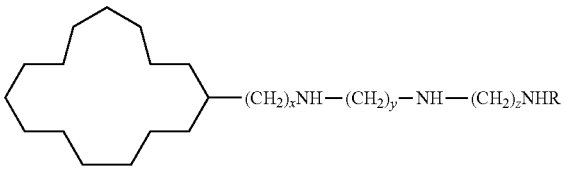

wherein x=0-6;

wherein y=3 or 4 or 5; and wherein z=3 or 4 or 5;

R=acyl, or alkyl, or a pharmaceutically acceptable salt thereof.

7. The compound of claim 6, wherein x=1, y=z=3 and R=acetyl; or x=1, y=z=3 and R=Me.

8. A compound represented by the formula:

(V)

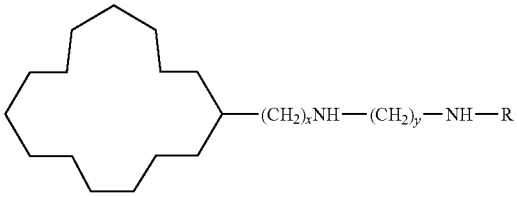

wherein x=0-6;

wherein y=2-8;

R=hydrogen, acyl, or alkyl, or a pharmaceutically acceptable salt thereof.

9. The compound of claim 8, wherein x=1, y=3 and R=acetyl; or x=1, y=3 and R=methyl; or x=1, y=3 and R=ethyl, or a pharmaceutically acceptable salt thereof.

* * * * *